US006890719B2

(12) United States Patent
Lu et al.

(10) Patent No.: US 6,890,719 B2
(45) Date of Patent: May 10, 2005

(54) FLUORESCENCE BASED BIOSENSOR

(75) Inventors: Yi Lu, Champaign, IL (US); Juewen Liu, Urbana, IL (US)

(73) Assignee: The Board of Trustess of the University of Illinois, Urbana, IL (US)

( * ) Notice: Subject to any disclaimer, the term of this patent is extended or adjusted under 35 U.S.C. 154(b) by 0 days.

(21) Appl. No.: 10/144,094

(22) Filed: May 10, 2002

(65) Prior Publication Data

US 2004/0023216 A1 Feb. 5, 2004

(51) Int. Cl.[7] .......................... C12Q 1/68; C12P 19/34; C12M 1/34; G01N 33/00; C07H 21/02
(52) U.S. Cl. ...................... 435/6; 435/91.1; 435/287.2; 436/94; 436/800; 536/23.1
(58) Field of Search ...................... 435/6, 183, 287.2, 435/91.1, 91.2; 436/94; 536/23.1, 24.31, 25.32

(56) References Cited

U.S. PATENT DOCUMENTS 6,451,535 B1    9/2002    Jenne et al.

FOREIGN PATENT DOCUMENTS

| DE | 19915141 | 9/2000 |
|---|---|---|
| WO | WO 99/47704 | 9/1999 |
| WO | WO 02/00006 | 1/2002 |

OTHER PUBLICATIONS

Merriam–Webster OnLine; definition of "ion," accessed and printed Mar. 7, 2004.*
Jenne, A.; Gmelin, W.; Raffler, N.; Famulok, M. Real–time Characterization of Ribozymes by Fluorescence Resonance Energy Transfer (FRET). *Angewandte Chemie, International Edition, Verlag Chemie.* May 3, 1999, vol. 38, No. 9, 1300–1303.*
Jenne, A.; Hartig, J. S.; Piganeau, N.; Tauer, A.; Samarsky, D. A.; Green, M. R.; Davies, J.; Famoluk, F. Rapid Identification and Characterization of Hammerhead–Ribozyme Inhibitors Using Fluorescence–Based Technology. *Nature Biotechnology.* Jan. 1, 2002, vol. 19, No. 1, 56–61.*
Singh, K. K.; Rucker, T.; Hanne, A.; Parwaresch, R.; Krupp, G. Fluorescence Polarization for Monitoring Ribozyme Reactions in Real–Time. *Biotechniques.* Aug. 2000, vol. 29, No. 2, 344–351.*
Bogden, J.D.; Louria, D.B. *Bull. Environ. Contam. Toxicol.* 1975, 14:289–94.
Breaker, R. R.; Joyce, G. F. *Chem. Biol.* 1995, 2, 655–660.
Breaker, R.R. & Joyce, G.F. A DNA enzyme that cleaves RNA. *Chem. Biol.* 1, 223–229 (1994).
Breaker, R.R. DNA enzymes. *Nat. Biotechnol.* 15, 427–431 (1997).

Cadwell, R. C.; Joyce, G. F. *PCR Methods Appl.* 1992, 2, 28–33.
Cadwell, R. C.; Joyce, G. F. *PCR Methods Appl.* 1994, 3, S136–S140.
Carmi, N., Shultz, L.A. & Breaker, R.R. In vitro selection of self–cleaving DNAs. *Chem. Biol.* 3, 1039–1046 (1996).
Chapman, K. B.; Szostak, J. W. *Curr. Opin. Struct. Biol.* 1994, 4, 618–622.
Ciesiolka, J.; Gorski, J.; Yarus, M. *RNA* 1995, 1, 538–550.
Ciesiolka, J.; Yarus, M. *RNA* 1996, 2, 785–793.
Conaty, J.; Hendry, P.; Lockett, T. *Nucleic Acids Res.* 1999, 27, 2400–2407.
Conn, M. M.; Prudent, J. R.; Schultz, P. G. *J. Am. Chem. Soc.* 1996, 118, 7012–7013.
Cuenoud, B. & Szostak, J.W. A DNA metalloenzyme with DNA ligase activity. *Nature* 375, 611–614 (1995).
Czarnik, A.W. Desperately seeking sensors. *Chem. Biol.* 2, 423–428 (1995).
Dai, X.; De Mesmaeker, A.; Joyce, G. F. *Science* 1995, 267, 237–240.
Deo, S. & Godwin, H.A. A Selective, Ratiometric Fluorescent Sensor for $Pb^{2+}$. *J. Am. Chem. Soc.* 122, 174–175 (2000).
Didenko, V.V., *BioTechniques* 2001, 31:1106–18.
Earnshaw & Gait, "Modified Oligoribonucleotides as site–specific probes of RNA structure and function," *Biopolymers* (John Wiley & Sons, Inc.) 48:39–55, 1998.
Ekland, E. H.; Szostak, J. W.; Bartel, D. P. *Science* 1995, 269, 364–370.
Ekland, E. H.; Bartel, D. P. *Nature* 1996, 382, 373–376.
Famulok, M. *Curr. Opin Struct. Biol.* 1999, 9, 324–329.
Faulhammer, D.; Famulok, M. *Angew. Chem., Int. Ed. Engl.* 1997, 35, 2837–2841.
Fodor, S.P.A., Read, J.L., Pirrung, M.C., Stryer, L., Lu, A.T. & Solas, D. (1991). Light–directed, spatially addressable parallel chemical synthesis. *Science* 251: 767–773.
Frank, D. N.; Pace, N. R. *Proc. Natl. Acad. Sci. U. S. A.* 1997, 94, 14355–14360.
Geyer, C. R.; Sen, D. *Chem. Biol.* 1997, 4, 579–593.
Godwin, H.A. & Berg, J.M. A Fluorescent Zinc Probe Based on Metal–Induced Peptide Folding. *J. Am. Chem. Soc.* 118, 6514–6515 (1996).
Guschin, D., Yershov, G., Zaslavsky, A., Gemmell, A., Shick, V., Proudnikov, D., Arenkov, P. & Mirzabekov, A. (1997). Manual manufacturing of oligonucleotide, DNA, and protein microchips. *Anal. Biochem.* 250: 203–211.
Hennrich, G.; Sonnenschein, H.; Resch–Genger, U. *J. Am. Chem. Soc.* 1999, 121, 5073–5074.
Illangasekare, M.; Yarus, M. *J. Mol. Biol.* 1997, 268, 631–639.

(Continued)

*Primary Examiner*—Bradley L. Sisson
(74) *Attorney, Agent, or Firm*—Evan Law Group LLC

(57) ABSTRACT

A novel biosensor comprises at least one fluorophore and at least two quenchers, and is capable of selectively and specifically detecting the presence of an ion in the presence of other ions.

16 Claims, 14 Drawing Sheets

OTHER PUBLICATIONS

Figure 1A:
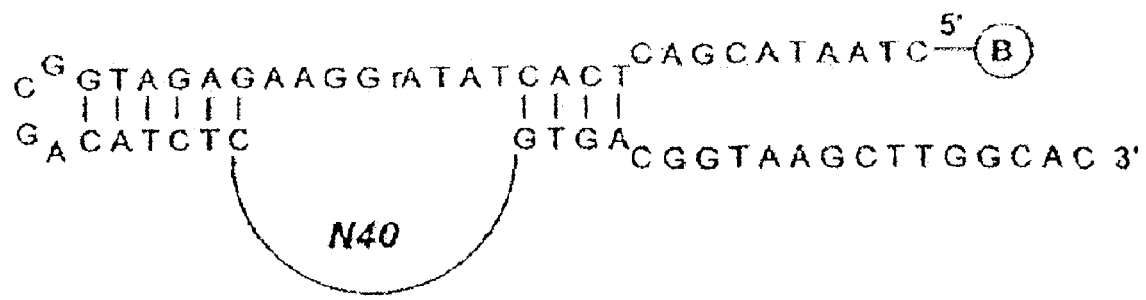

Imperiali, B., Pearce, D.A., Sohna, J.-E., Walkup, G. & Torrado, A. Peptide platforms for metal ion sensing. *Proc. SPIE–Int. Soc. Opt. Eng.* 3858, 135–143 (1999).

Jhaveri, et al., Designed Signaling Aptamers that Transduce Molecular Recognition to Changes in Fluorescence Intensity, *Journal of the American Chemical Society;* 2000; 122(11); 2469–2473.

Joos, B., Kuster, H. & Cone, R. (1997). Covalent attachment of hybridizable oligonucleotides to glass supports. *Anal. Biochem.* 247: 96–101.

Joyce, G. F. *Curr. Opin. Struct. Biol.* 1994, 4, 331–336.

Koizumi, M.; Soukup, G. A.; Kerr, J. N. Q.; Breaker, R. R. *Nat. Struct. Biol.* 1999, 6, 1062–1071.

Lee, M., & Walt, D. R. A fiber–optic microarray biosensor using aptamers as receptors. *Anal Biochem* 282(1):142–146, 2000.

Lehman, N.; Joyce, G.F. *Nature* 1993, 361, 182–185.

Li, J., Zheng, W., Kwon, A.H. & Lu, Y. In vitro selection and characterization of a highly efficient Zn(II)–dependent RNA–cleaving deoxyribozyme. *Nucleic Acids Res.* 28, 481–488 (2000).

Li, Y.; Sen, D. *Nat. Struct. Biol.* 1996, 3, 743–747.

Li, Y.; Breaker, R. R. *Proc. Natl. Acad. Sci. U. S. A.* 1999, 96, 2746–2751.

Li, Y.; Liu, Y.; Breaker, R. R. *Biochemistry* 2000, 39, 3106–3114.

Lohse, P.A.; Szostak, J. W. *Nature* 1996, 381, 442–444.

Lorsch, J. R.; Szostak, J. W. *Nature* 1994, 371, 31–36.

Marcus, A.H.; Elias, R.W. *ASTM Spec. Tech. Publ.* 1995, *STP 1226:* 12–23.

Miyawaki, A., et al. Fluorescent indicators for $Ca^{2+}$ based on green fluorescent proteins and calmodulin. *Nature* 388, 882–887 (1997).

O'Donnel–Maloney, M.J., Tang, K., Koester, H., Smith, C.L. & Cantor, C.R. (1997). High–Density, Covalent Attachment of DNA to Silicon Wafers for Analysis by MALDI–TOF Mass Spectrometry. *Anal. Chem.* 69:2438–2443.

Oehme, I. & Wolfbeis, O.S. Optical sensors for determination of heavy metal ions. *Mikrochim. Acta* 126, 177–192 (1997).

Pan, T. & Uhlenbeck, O.C. A small metalloribozyme with a two–step mechanism. *Nature* 358, 560–563 (1992).

Pan, T.; Dichtl, B.; Uhlenbeck, O. C. *Biochemistry* 1994, 33, 9561–9565.

Pearce, D. A.; Walkup, G. K.; Imperiali, B. *Bioorg. Med. Chem. Lett.* 1998, 8, 1963–1968.

Pease, A.C., Solas, D., Sullivan, E.J., Cronin, M.T., Holmes, C.P. & Fodor, S.P.A. (1994). Light–generated oligonucleotide arrays for rapid DNA sequence analysis. *Proc. Natl. Acad. Sci. U. S. A.* 91: 5022–5026.

Piccirilli, J. A.; McConnell, T. S.; Zaug, A. J.; Noller, H. F.; Cech, T. R. *Science* 1992, 256, 1420–1424.

Pley, H. W.; Flaherty, K. M.; McKay, D. B. *Nature* 1994, 372, 68–74.

Potyrailo, R.A., Conrad, R.C., Ellington, A.D. & Hieftje, G.M. (1999). Adapting Selected Nucleic Acid Ligands (Aptamers) to Biosensors. *Anal. Chem.* 70: 3419–3425.

Prudent, J. R.; Uno, T.; Schultz, P. G. *Science* 1994, 264, 1924–1927.

Rabinowitz, M.; Leviton, A.; Bellinger, D. *Am. Jour. Public Health Field.* 1985, Apr. 75: 403–4.

Robertson, M. P.; Ellington, A. D. *Nat. Biotechnol.* 1999, 17, 62–66.

Robertson, M. P.; Ellington, A. D. *Nucleic Acids Res.* 2000, 28, 1751–1759.

Roth, A.; Breaker, R. R. *Proc. Natl. Acad. Sci. U. S. A.* 1998, 95, 6027–6031.

Rurack, K., Kollmannsberger, M., Resch–Genger, U. & Daub, J. A Selective and Sensitive Fluoroionophore for HgII, AgI, and CuII with Virtually Decoupled Fluorophore and Receptor Units. *J. Am. Chem. Soc.* 122, 968–969 (2000).

Santoro, S. W.; Joyce, G. F. *Proc. Natl. Acad. Sci. U. S. A.* 1997, 94, 4262–4266.

Santoro, S.W., Joyce, G.F., Sakthivel, K., Gramatikova, S. & Barbas, C.F., III RNA Cleavage by a DNA Enzyme with Extended Chemical Functionality. *J. Am. Chem. Soc.* 122, 2433–2439 (2000).

Schwartz, J.; Levin, R. *Env. Research Field.* 1991, Feb. 54: 1–7.

Scott, W. G.; Finch, J. T.; Klug, A. *Cell* 1995, 81, 991–1002.

Tang and Breaker, *Proc. Natl. Acad. Sci. USA,* 97, 5784–5789 (2000).

Tarasow, T. M.; Tarasow, S. L.; Eaton, B. E. *Nature* 1997, 389, 54–57.

Thompson, R.B., Maliwal, B.P., Feliccia, V.L., Fierke, C.A. & McCall, K. Determination of Picomolar Concentrations of Metal Ions Using Fluorescence Anisotropy: Biosensing with a "Reagentless" Enzyme Transducer. *Anal. Chem.* 70, 4717–4723 (1998).

Tsang, J.; Joyce, G. F. *Methods Enzymol.* 1996, 267, 410–426.

Tsien, R.Y. Fluorescent and photochemical probes of dynamic biochemical signals inside living cells. in *Fluorescent Chemosensors for Ion and Molecule Recognization* (ed. Czarnik, A.W.) 130–46 (American Chemical Society, Washington, DC, 1993).

Tuerk, C.; Gold, L. *Science* 1990, 249, 505–510.

Tyagi S; Kramer, F.R. *Nat. Biotechnol.* 1996 14, 303–308.

Tyagi, S.; Bratu, D.P.; Kramer, F.R., *Nat. Biotechnol.,* 1998, 16:49–53.

Uphoff, K. W.; Bell, S. D.; Ellington, A. D. *Curr. Opin. Struct. Biol.* 1996, 6, 281–288.

Vaish, N. K.; Heaton, P. A.; Fedorova, O.; Eckstein, F. *Proc. Natl. Acad. Sci. U. S. A.* 1998, 95, 2158–2162.

Walkup, G.K. & Imperiali, B. Design and Evaluation of a Peptidyl Fluorescent Chemosensor for Divalent Zinc. *J. Am. Chem. Soc.* 118, 3053–3054 (1996).

Wecker, M.; Smith, D.; Gold, L. *RNA* 1996, 2, 982–994.

Wiegand, T. W.; Janssen, R. C.; Eaton, B. E. *Chem. Biol.* 1997, 4, 675–683.

Wilson, C.; Szostak, J. W. *Nature* 1995, 374, 777–782.

Winkler, J.D., Bowen, C.M. & Michelet, V. Photodynamic Fluorescent Metal Ion Sensors with Parts per Billion Sensitivity. *J. Am. Chem. Soc.* 120, 3237–3242 (1998).

Wittmann, C., Riedel, K. & Schmid, R.D. Microbial and Enzyme sensors for environmental monitoring, *Handb. Biosens. Electron. Noses ,* 299–332 (1997).

Zhang, B.; Cech, T. R. *Nature* 1997, 390, 96–100.

Zillmann, M.; Limauro, S. E.; Goodchild, J. *RNA* 1997, 3, 734–747.

\* cited by examiner

```
Zn-DNA

5'- CTGCAGAATTCTAATACGACTCACTATAGGAAGAGATGGCGAC

Class I (used for reselection)
#5,6,7,9,21,25,29,43,47
        ATCTC TTTTGTCAGCGACTCGAAATAGTGTGTTGAAGCAGCTCTA GTGAC Class II
2,10,17,20,24,31,37,39
        AGCCA -TAGTTCTACCAGCGGTTCGAAATAGTGAAGTGTTCGTGA CTATC
#3      GGCCA -TAGTTCTACCAGCGGTTCGAAATAGTGAAATGTTCGTGA CTATC
4      GCCAGATTAGTTCTACCAGCGGTTCGAAATAGTGAAATGTTCGTGA CTATC Class III
15,18,19,34,35,38,50
        ATCTC CAAAGATGCCAGCATGCTATTCTCCGAGCCGGTCGAAATA GTGAC
14     ATCTC CAAAGATGCCTGCATGCTATTCTCCGAGCCGGTCGAAATA GTGAC Unclassified
36     ATCTC GTCTCCGAGCCGGTCGAAATAGTCAGGTGTTTCTATTCGG GTGAC
#40     ATCAC CTTCTCCGAGCCGGTCGAAATAGTAGTTTTTAGTATATCT GTGAC
#42     ATCTC AGGTGTTGGCTGCTCTCGCGGTGGCGAGAGGTAGGGTGAT GTGAC

GGTAAGCTTGGCAC-3'
```

FIG. 2

```
Co-DNA

5'-CTGCAGAATTCTAATACGACGCACTATAGGAAGAGATGGCGAC

Class I (used for reselection)
#18,15,34
        ATCTC TTGTATTAGCTACACTGTTAGTGGATCGGGTCTAATCTCG  GTGAC
#1      GTCTC TTGTATTAGCTACACTGTTAGTGGATCGGGTCTAATCTCG  GTGAC
#25     ATCTC CTGTATTAGCTACACTGTTAGTGGATCGGGTCTAATCTCG  GTGAC
16     ATCTC TTGTATTAGCTACACTGTTAGTGGGAACGTTATCAT-TCG  GTGAC Class II
2,4,7,23,26
        ATCTC TTGACCCAAGAAGGGGTGTCAATCTAATCCGT CAACCATG
#8      ATCTC TTGACCCAAGAAGGGGTGTCAATCAAATCCGT CAACCATG
#17     ATCTC TTGACCCAAGAAGGGGTGTCAATCTAATCCGTACAACCATG ACGGTAAG
27     ATCTC TTGACCCAAGAAGGGGTGTCAATCTAATCCGT CAAGGATG  CGGTAAG Class III
5      ATCTC AGGTGTTGGCTGCTCCCGCGGTGGCGGGAGGTAGGGTGAT  GTGAC
#11     ATCTC AGGTGTTGGCATCTCCCGCGGTGGCGAGAGGTAGGGTGAT  GTGAC
6      ATCTC ACGTGTTGGCTGCTCTCGCGGTGGCGAGAGGTAGGGTCAT  GTGAC Unclassified
21     ATCTC GCAGTCGAAGCTTCACTGTTAGTGCGGACGGGTAGACTTC  GTGAC
#29     ATTTC TTCTGAATCCTCAATGTTAGTGGACCTAGTCGTAGTCGAT  GTGAC
#12     ATCTC GGAGCCAGTTAGCATAATCTTCTGAATCCTCAATGTTAGT  GTGAC
#10     ATCTC GGTGTTGGCTGGATAGAGCCGGTAGGCCCTATCGTAGGGT  GTGAC
#1      GTCTC TTTTGTCCGCGACTCGAAATAGTGTGTTGAAGCAGCTCTA  GTGAC
#28     AGCCA TAGTTCTACCAGCGGTTCGAAATAGTGAAGTGTTCGTGACTATCG  GTAA

GGTAAGCTTGGCAC-3'
```

FIG. 3

|     | 1 | 10 | 20 | 30 | 40 | $k_{obs}$ (min$^{-1}$) |
|-----|---|----|----|----|----|----|

```
              1         10        20        30        40    k_obs(min⁻¹)
              TTTTGTCAGCGACTCAAATAGTGTCTGAAGCAGCTCT
#1,27
#10                                         C     T   A
#27                                         A     T   C
#5                                 A A    C  CA   C
#6,7                              TA A                        0.0996
#17                               A  A   AAG   G       G      0.16
#22                               A  GG   C                   0.1314
#31                               A  A    C
#33                               A  A
#8                                A    A      G G    G        0
#19         T         A           A           G A             0.0932
#24                               CA
#28                                 C    A
#20                              C G     A         C          0.156
#30                                       A    T
#9                                        AC
#18                                          T
#32                                                CG         0.108
#11
#13                                       A    AG
#14                                       A              A
#21        G  A    T        T  T         G              C     0.128/0.101
#26       G C     ST         TA         C         G    A      0.177
#34          T                                    G
#40         C C       AA                  C              A
#25        A          T                      E         C
#15                   T      -            T       A    C
```

FIG. 4

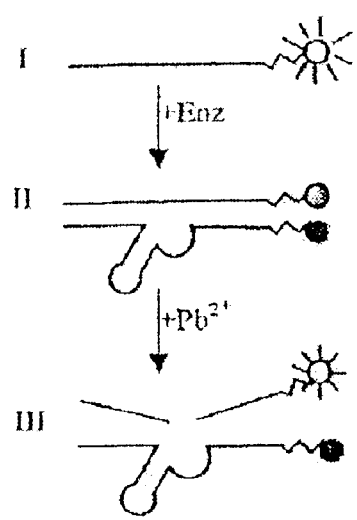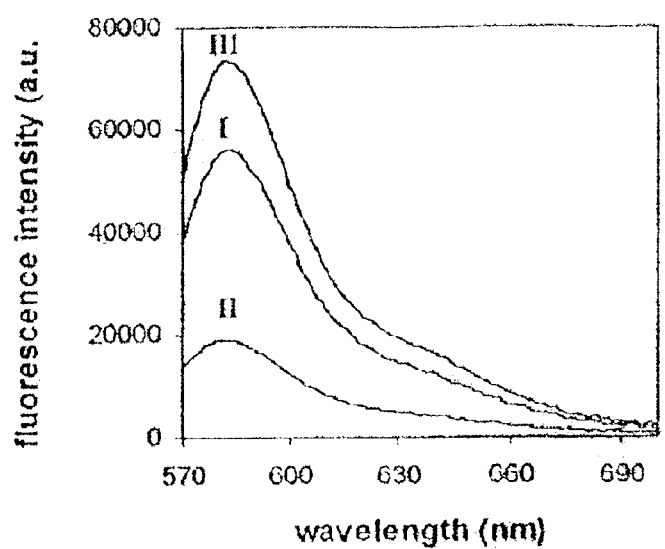
FIG. 8

FIG. 9A
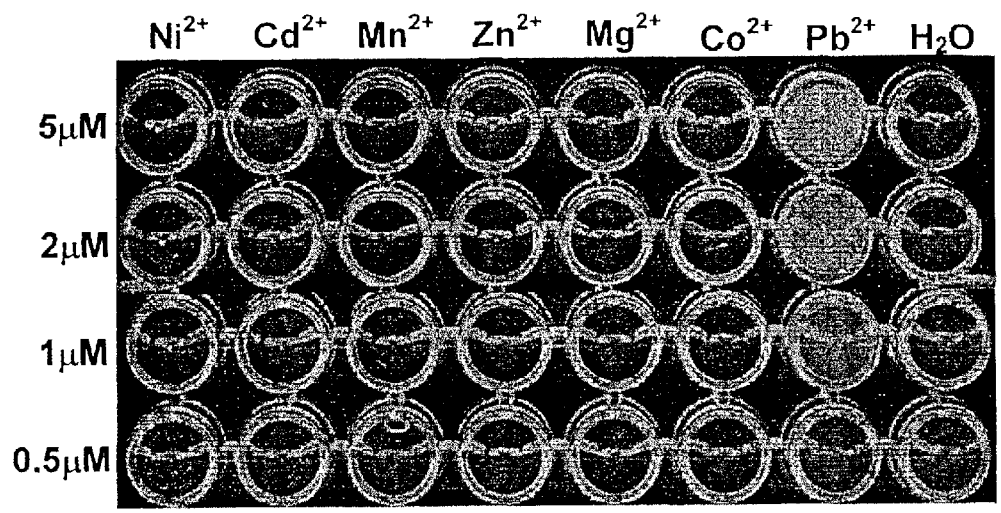
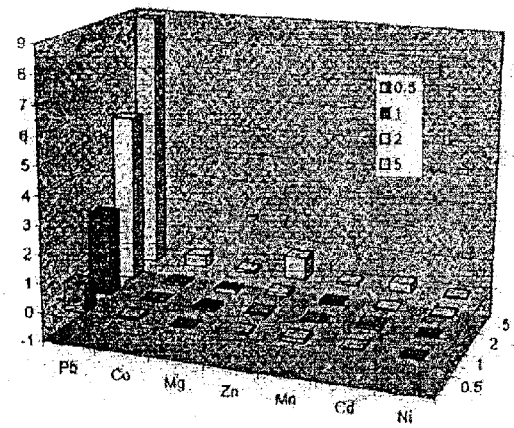
FIG 9B
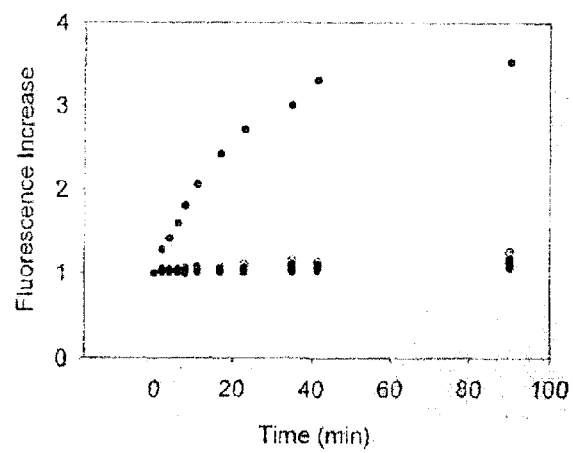
FIG 9C

HYPOTHETICAL SAMPLE RESULT

SEQUENCE LISTING

<160> NUMBER OF SEQ ID NOS: 84

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      Trans-cleaving deoxyribozyme 17E

<400> SEQUENCE: 1
catctcttct ccgagccggt cgaaatagtg agt                                33

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate

<400> SEQUENCE: 2
actcactata ggaagagatg                                               20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 3
gtgccaagct taccg                                                    15

```
<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 4
ctgcagaatt ctaatacgac tcactatagg aagagatggc gac          43

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule:
      Primer

<400> SEQUENCE: 5
gggacgaatt ctaatacgac tcactata                            28

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence:
      DNA Template
<220> FEATURE:
<221> NAME/KEY: modified_base
<222> LOCATION: (20)..(59)
<223> OTHER INFORMATION: variable nucleotides

<400> SEQUENCE: 6
gtgccaagct taccgtcacn nnnnnnnnnn nnnnnnnnnn nnnnnnnnnn nnnnnnnng    60 agatctcgcc atctcttcct atagtgagtc gtattag                             97

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Variant of
      deoxyribozyme named 17E1

<400> SEQUENCE: 7
catctctttt gtcagcgact cgaaatagtg agt                      33

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Zn-DNA
<220> FEATURE:
<221> NAME/KEY: modified_base
<222> LOCATION: (2)..(4)
<223> OTHER INFORMATION: variable base complementary to positions 8-10
<220> FEATURE:
<221> NAME/KEY: modified_base
<222> LOCATION: (8)..(10)
<223> OTHER INFORMATION: variable base complementary to positions 2-4

<400> SEQUENCE: 8
tnnnagcnnn tcgaaatagt                                     20
```

```
<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Zn-DNA
<220> FEATURE:
<221> NAME/KEY: modified_base
<222> LOCATION: (2)..(4)
<223> OTHER INFORMATION: variable base complementary to positions 8-10
<220> FEATURE:
<221> NAME/KEY: modified_base
<222> LOCATION: (8)..(10)
<223> OTHER INFORMATION: variable base complementary to positions 2-4

<400> SEQUENCE: 9
tnnnagcnnn acgaa                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Class II
      Co-DNA

<400> SEQUENCE: 10
acccaagaag gggtg                                                    15

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Rh-17DDS

<400> SEQUENCE: 11
actcactata ggaagagatg                                               20

<210> SEQ ID NO 12
<211> LENGTH: 97
<212> TYPE: DNA
<213> ORGANISM: Artificial Sequence
<220> FEATURE:
<223> OTHER INFORMATION: Description of Artificial Sequence: Synthetic
      chimeric substrate
<220> FEATURE:
<223> OTHER INFORMATION: Description of Combined DNA/RNA Molecule:
      Synthetic chimeric substrate
<220> FEATURE:
<221> NAME/KEY: modified_base
<222> LOCATION: (39)..(78)
<223> OTHER INFORMATION: variable nucleotides

<400> SEQUENCE: 12
ctaatacgac tcactatagg aagagatggc gacatctcnn nnnnnnnnn nnnnnnnnn     60 nnnnnnnnnn nnnnnnnngt gacggtaagc ttggcac                            97

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Zn-DNA

<400> SEQUENCE: 13
ctgcagaatt ctaatacgac tcactatagg aagagatggc gac                     43
```

```
<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Zn-DNA

<400> SEQUENCE: 14
atctcttttg tcagcgactc gaaatagtgt gttgaagcag ctctagtgac         50

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Zn-DNA

<400> SEQUENCE: 15
agccatagtt ctaccagcgg ttcgaaatag tgaagtgttc gtgactatc          49

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Zn-DNA

<400> SEQUENCE: 16
ggccatagtt ctaccagcgg ttcgaaatag tgaaatgttc gtgactatc          49

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Zn-DNA

<400> SEQUENCE: 17
gccagattag ttctaccagc ggttcgaaat agtgaaatgt tcgtgactat c       51

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Zn-DNA

<400> SEQUENCE: 18
atctccaaag atgccagcat gctattctcc gagccggtcg aaatagtgac         50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Zn-DNA

<400> SEQUENCE: 19
atctccaaag atgcctgcat gctattctcc gagccggtcg aaatagtgac         50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Zn-DNA
```

```
<400> SEQUENCE: 20
atctcgtctc cgagccggtc gaaatagtca ggtgtttcta ttcgggtgac         50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Zn-DNA

<400> SEQUENCE: 21
atcaccttct ccgagccggt cgaaatagta gtttttagta tatctgtgac         50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Zn-DNA

<400> SEQUENCE: 22
atctcaggtg ttggctgctc tcgcggtggc gagaggtagg gtgatgtgac         50

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Zn-DNA

<400> SEQUENCE: 23
ggtaagcttg gcac                                                14

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Co-DNA

<400> SEQUENCE: 24
ctgcagaatt ctaatacgac gcactatagg aagagatggc gac                43

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 25
atctcttgta ttagctacac tgttagtgga tcgggtctaa tctcggtgac         50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 26
gtctcttgta ttagctacac tgttagtgga tcgggtctaa tctcggtgac         50
```

```
<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 27
atctcctgta ttagctacac tgttagtgga tcgggtctaa tctcggtgac            50

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Co-DNA

<400> SEQUENCE: 28
atctcttgta ttagctacac tgttagtggg aacgttatca ttcggtgac             49

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Co-DNA

<400> SEQUENCE: 29
atctcttgac ccaagaaggg gtgtcaatct aatccgtcaa ccatg                 45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Co-DNA

<400> SEQUENCE: 30
atctcttgac ccaagaaggg gtgtcaatca aatccgtcaa ccatg                 45

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Co-DNA

<400> SEQUENCE: 31
atctcttgac ccaagaaggg gtgtcaatct aatccgtaca accatgacgg taag       54

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Co-DNA

<400> SEQUENCE: 32
atctcttgac ccaagaaggg gtgtcaatct aatccgtcaa ggatgcggta ag         52

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Co-DNA
```

<400> SEQUENCE: 33
atctcaggtg ttggctgctc ccgcggtggc gggaggtagg gtgatgtgac          50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 34
atctcaggtg ttggcatctc ccgcggtggc gagaggtagg gtgatgtgac          50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 35
atctcaggtg ttggctgctc tcgcggtggc gagaggtagg gtcatgtgac          50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 36
atctcgcagt cgaagcttca ctgttagtgc ggacgggtag acttcgtgac          50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 37
atttcttctg aatcctcaat gttagtggac ctagtcgtag tcgatgtgac          50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 38
atctcggagc cagttagcat aatcttctga atcctcaatg ttagtgtgac          50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 39
atctcggtgt tggctggata gagccggtag gccctatcgt agggtgtgac          50

```
<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Co-DNA

<400> SEQUENCE: 40
gtctcttttg tccgcgactc gaaatagtgt gttgaagcag ctctagtgac           50

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: Co-DNA

<400> SEQUENCE: 41
agccatagtt ctaccagcgg ttcgaaatag tgaagtgttc gtgactatcg gtaa      54

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Co-DNA

<400> SEQUENCE: 42
ggtaagcttg gcac                                                  14

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 43
ttttgtcagc gactcgaaat agtgtgttga agcagctcta                      40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 44
ttttgtcagc gactcgaaat agtgtgttga agccgctcta                      40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 45
ttttgtcagc gactcgaaat agtgtattgc agtagatcta                      40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Zn-DNA
```

```
<400> SEQUENCE: 46
ttttgtcagc gactcgaaat agtgtgttac agttgcccta                    40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 47
ttttgtcagc gactcgaaat agagagtcga cacacctctc                    40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 48
ttttgtcagc gactcgaaat agttagttga accagctctc                    40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 49
ttttgtcagc gactcgaaat agtgagtaag aggagctatc                    40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 50
ttttgtcagc gactcgaaat agtgagggga aacagctctc                    40

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Zn-DNA

<400> SEQUENCE: 51
ttttgtcagc gactcgaaat agttagttga acacctctc                     39

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 52
ttttgtcagc gactcgaaat attgagttga agcagatctc                    40
```

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 53
ttttgtcagc gacacgaaat agtgagttga ggcggcgctg        40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 54
tttttgcagc gacacgaaat agttagttga agaagctctt        40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 55
ttttgtcagc gactcgaaat agtcagttgt agcagctctt        40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 56
ttttgtcagc gactcgaaat agtgcgtaga accagctctc        40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 57
ttttgtcagc gacacgaaat agtgcggtgt atctgccctc        40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 58
ttttgtcagc gacacgaaat agtgtgatgt agtagctctc        40

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Zn-DNA -continued

```
<400> SEQUENCE: 59
ttttgtcagc gacacgaaat agtgtgacga atcatctc                              38

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Zn-DNA

<400> SEQUENCE: 60
ttttgtcagc gacacgaaat agtgtgttta agcgctctc                             39

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 61
ttttgtcagc gacacgaaat agtgtgttga agcacgtctc                            40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 62
ttttgtcagc gactcgaaat agtttgttga agcagctctc                            40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 63
ttttgtcagc gactcgaaat agtgtattac agcagctctc                            40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 64
ttttgtcagc gactcgaaat agtgtgttga aacagctatc                            40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 65
ttgtgcatgc tactcgtaat tgtgtctcga agcagctctc                            40
```

```
<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 66
gtcagtcagg tactcgaaaa atagtgttca agccgctgtc                              40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 67
tttttgcagc gactcgaaag attgtgttga ggcggctatc                              40

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 68
ttctctcagc gactaaaaat agtgtgttga agccctctc                               40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Zn-DNA

<400> SEQUENCE: 69
tattgtcagt gacccaaaat agtatgttga agcagctctg                              40

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Zn-DNA

<400> SEQUENCE: 70
ttttgtcagc tactgaaata gtgttttgaa gaagtcctg                               39

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 71
tcactatagg aagag                                                         15
```

```
<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 72
ctcttcagcg atccggaacg gcacccatgt tagtga                              36

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 73
tcactataag aagagatgg                                                 19

<210> SEQ ID NO 74
<211> LENGTH: 37
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 74
acacatctct gaagtagcgc cgccgtatag tgacgct                             37

<210> SEQ ID NO 75
<211> LENGTH: 17
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 75
ggagagagau gggugcg                                                   17

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 76
cgcacccagg ctagctacaa cgactctctc c                                   31
```

```
<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 77
aaguaacuag agaugga                                                  17

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 78
cgcaccctcc gagccggacg aagttactt                                     29

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 79
ctcactatag gaagagatg                                                19

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 80
catctcttaa cggggctgtg cggctaggaa gtaatagtga g                       41

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 81
actcactata ggaagagatg                                               20
```

```
<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:
      Synthetic chimeric substrate
<220> FEATURE:
<223> OTHER INFORMATION: Description of Combined DNA/RNA Molecule:
      Synthetic chimeric substrate

<400> SEQUENCE: 82
catctcttct ccgagccggt cgaaatagtg agt                              33

<210> SEQ ID NO 83
<211> LENGTH: 107
<212> TYPE: DNA
<213> ORGANISM: Artificial Sequence
<220> FEATURE:
<223> OTHER INFORMATION: Description of Artificial Sequence: Predicted
      secondary structure of the G3 deoxyribozyme
<220> FEATURE:
<221> NAME/KEY: modified_base
<222> LOCATION: (67)
<223> OTHER INFORMATION: variable nucleotide
<220> FEATURE:
<221> NAME/KEY: modified_base
<222> LOCATION: (69)..(74)
<223> OTHER INFORMATION: variable nucleotide
<220> FEATURE:
<221> NAME/KEY: modified_base
<222> LOCATION: (80)..(82)
<223> OTHER INFORMATION: variable nucleotide
<220> FEATURE:
<221> NAME/KEY: modified_base
<222> LOCATION: (85)..(89)
<223> OTHER INFORMATION: variable nucleotide

<400> SEQUENCE: 83
gggacgaatt ctaatacgac tcactatagg aagagatggc gacaactctt tacccaagaa    60
ggggtgngnn nnnngctacn nnatnnnnnt gacggtagct tggcacc                 107

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Co-DNA

<400> SEQUENCE: 84
cactatagga agagatggcg acatctcttg acccaagaag gggtg                   45
```

FLUORESCENCE BASED BIOSENSOR

FEDERALLY SPONSORED RESEARCH OR DEVELOPMENT

The U.S. Government may have rights in the present invention pursuant to the terms of grant number DEFG02-01ER63179 awarded by the Department of Energy.

BACKGROUND

Many metals pose a risk as environmental contaminants. A well-known example is lead. Low level lead exposure can lead to a number of adverse health effects, with as many as 9–25% of pre-school children presently at risk. Approximately twenty-two million old houses in the United States alone have lead paint (Schwartz & Levin, 1991; Rabinowitz et al., 1985). Although leaded paints and gasoline have been banned, lead can accumulate in soils or sediments for long periods of time (Marcus & Elias, 1995; Bogden & Louria, 1975). The level of lead in the blood considered toxic is $\geq 10$ $\mu g/dL$ (480 nM). Current methods for lead analysis, such as atomic absorption spectrometry, inductively coupled plasma mass spectrometry, and anodic stripping voltammetry, are complex, expensive and often require sophisticated equipment, sample pre-treatment and skilled operators.

Simple, rapid, inexpensive, selective and sensitive methods that permit real time detection of $Pb^{2+}$ and other metal ions are very important in the fields of environmental monitoring, clinical toxicology, wastewater treatment, and industrial process monitoring and can lead to preventative measures or at least lower risks associated with metal contaminants. Furthermore, methods are needed for monitoring free or bioavailable, instead of total, metal ions in industrial and biological systems.

Fluorescence spectroscopy is a technique well suited for detection of very small concentrations of analytes. Fluorescence provides significant signal amplification, since a single fluorophore can absorb and emit many photons, leading to strong signals even at very low concentrations. In addition, the fluorescence time-scale is fast enough to allow real-time monitoring of concentration fluctuations. Fluorescent properties only respond to changes related to the fluorophore, and therefore can be highly selective. Also, fluorometers, for measuring fluorescence signals, are commercially available. Fluorescent detection is also compatible with fiber-optic technology and well suited for in vivo imaging applications. Several fluorescence-related parameters can be assessed for purposes of sensing, detecting, identifying or quantifying a target analyte, including fluorescence intensity, emission or excitation wavelength, fluorescence lifetime and anisotropy.

For example, bioaffinity sensors, labeled with fluorophores, have been used to detect DNA hybridization and single-nucleotide polymorphisms (Didenko, 2001). Specifically, molecular beacon, a DNA hairpin structure, is labeled with both a fluorophore and quencher (Tyagi & Kramer, 1996). In the absence of target DNA, the hairpin structure is closed and due to the close proximity of the fluorophore and quencher, fluorescence is quenched. However, in the presence of a complementary DNA strand, the hairpin secondary structure is destroyed and the fluorescence is released without quenching. Multiple DNA strands may be detected at the same time by placing a quencher on one end of the molecular beacon DNA strand and two fluorophores (a donor fluorophore and an acceptor fluorophore) on the other end (Tyagi & Kramer, 1998; 2000). This design, based on fluorescence resonance energy transfer (FRET), quenches fluorescence of the fluorophores in the absence of complementary DNA due to the hairpin structure being closed. However, upon hybridization of the molecular beacon and the complementary DNA, the secondary structure is destroyed and the donor fluorophore transfers energy to the acceptor fluorophore, resulting in fluorescence. Molecular beacon can be designed to target different DNA sequences by constructing complementary DNA strand hairpins, each with a different acceptor fluorophore, while keeping the donor fluorophore the same.

Biosensors, devices capable of detecting target ions using biological reactions, in contrast to bioaffinity sensors, can be modified to utilize fluorescence for detecting, identifying or quantifying target ions, which can act as catalysts of the biosensor. These modified biosensors, called fluorosensors, are highly sensitive. For example, many fluorescent chemosensors, including fluorophore-labeled organic chelators (Rurack, et al., 2000; Hennrich et al., 1999; Winkler et al., 1998; Oehme & Wolfbeis, 1997) and peptides (Walkup & Imperiali, 1996; Deo & Godwin, 2000; Pearce et al., 1998), have been developed for metal ion detection. These ion sensors are usually composed of an ion-binding motif and a fluorophore. Metal detection using these fluorescent chemosensors relies on the modulation of the fluorescent properties of the fluorophore by the metal-binding event. Detection limits on the level of micromolar and even nanomolar concentrations have been achieved for heavy metal ions including $Zn^{2+}$, $Cu^{2+}$, $Hg^{2+}$, $Cd^{2+}$ and $Ag^+$.

Recently, the molecular recognition and catalytic function of nucleic acids have been extensively explored. This exploration has led to the development of aptamers and nucleic acid enzymes, which can be used as biosensors. Aptamers are single-stranded oligonucleotides derived from an in vitro evolution protocol called systematic evolution of ligands by exponential enrichment (SELEX). Nucleic acid aptamers can selectively bind to non-nucleic acid targets, such as small organic molecules or proteins, with affinities as high as $10^{-14}$ M (Uphoff et al., 1996; Famulok, 1999). Most aptamers undergo a conformational change when binding their cognate ligands. With this property, several DNA and RNA aptamers have been engineered to sense L-adenosine or thrombin through an internally labeled fluorescent reporter group (Jhaveri et al., 2000). Thus, the conformational change in the aptamer upon binding leads to a change in fluorescence. Nucleic acid enzymes, molecules capable of catalyzing a chemical reaction, may be specifically designed through in vitro selection. (Breaker & Joyce, 1994; Breaker, 1997). Allosteric ribozymes (or aptazymes), which combine the features of both aptamer and catalytic RNA, also hold promise for sensing small molecules (Potyraito et al., 1998; Koizumi et al., 1999; Robertson & Ellington, 1999, 2000). Their reactivity is modulated through the conformational changes caused by the binding of small organic molecules to an allosteric aptamer domain. Therefore, the signal of ligand binding can be transformed into a signal related to chemical reaction.

SUMMARY

In a first aspect, the present invention is a method of detecting an ion in the presence of other ions, in a sample. The method comprises: forming a mixture of a nucleic acid enzyme including at least one quencher, a substrate and the sample, to produce a product; and detecting the presence of the product. The substrate is a nucleic acid sequence including a ribonucleotide, at least one quencher and at least one fluorophore.

In a second aspect, the present invention is a method of determining the concentration of an ion in the presence of other ions, in a sample, comprising: forming a mixture of a nucleic acid enzyme comprising at least one quencher, a substrate comprising a ribonucleotide, at least one quencher and at least one fluorophore, and the sample, to produce a product; and measuring the amount of product produced.

In a third aspect, the present invention is a biosensor, capable of detecting the presence of an ion in the presence of other ions, comprising: a nucleic acid enzyme which includes at least one quencher, and a substrate which includes a ribonucleotide, at least one quencher and at least one fluorophore.

A "nucleic acid enzyme" is a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made up of ribonucleotides, deoxyribonucleotides, or a combination of ribo- and deoxyribonucleotides.

A "sample" may be any solution that may contain an ion (before or after pre-treatment). The sample may contain an unknown concentration of an ion. For example, the sample may be paint that is tested for lead content. The sample may be diluted yet still remain a sample. The sample may be obtained from the natural environment, such as a take, pond, or ocean, an industrial environment, such as a pool or waste stream, a research lab, a common household, or a biological environment, such as blood. Of course, sample is not limited to the taking of an aliquot of solution but also includes the solution itself. For example, a biosensor may be placed into a body of water to measure for contaminants. In such instance, the sample may comprise the body of water or a particular area of the body of water. Alternatively, a solution may be flowed over the biosensor without an aliquot being taken. Furthermore, the sample may contain a solid or be produced by dissolving a solid to produce a solution. For example, the solution may contain soil from weapon sites or chemical plants.

"Measuring an amount of the product produced" includes measuring the result of the production of a product by an enzyme. For example, in an embodiment where the substrate comprises a quencher and fluorophore and the enzyme comprises a second quencher, and cleavage of the substrate by the enzyme leads to dissociation of the product from the enzyme, "measuring an amount of the product produced" includes detecting the increase of fluorescence. Thus, one is measuring the product by detecting its inability to quench fluorescence.

"Forming a mixture" includes placing the sample, a substrate and an enzyme in proximity such that an ion in the sample could be used as a cofactor. "Forming a mixture" includes such acts as pipetting a sample onto a solid support or into a tube or well containing the nucleic acid enzyme. Alternatively, the enzyme may be brought to the sample. For example, the enzyme may be placed into a stream to monitor for the presence of a contaminant.

BRIEF DESCRIPTION THE DRAWINGS

Figure 1B:
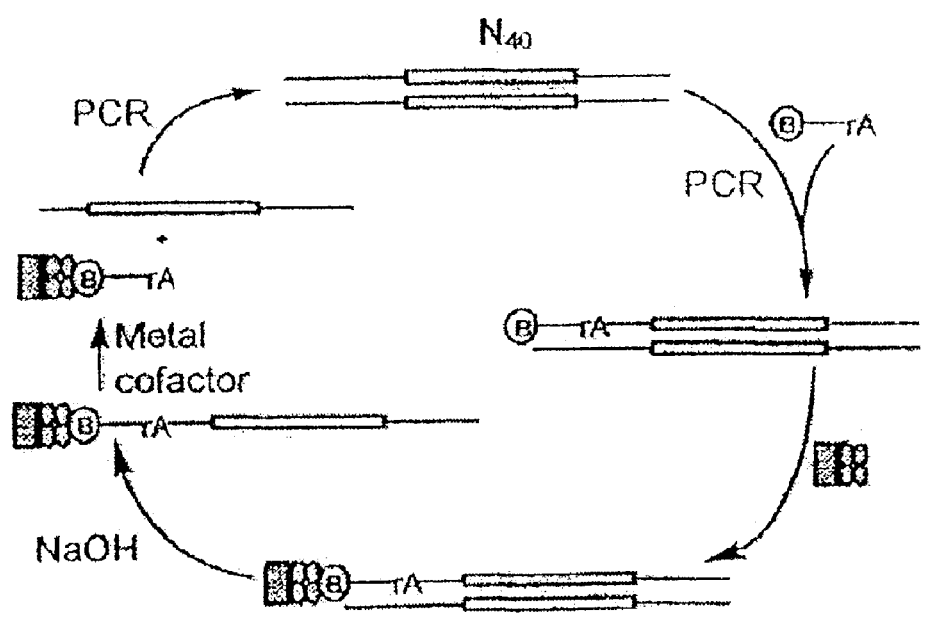

FIG. 1. Selection scheme for RNA-cleaving deoxyribozymes. FIG. 1A. (SEQ ID NO: 12) Starting pool of random-sequenced DNAs, engineered to contain two substrate-binding domains. Each member of the pool contains a 5'-terminal biotin (encircled B), a single embedded ribonucleotide (rA) and a 40-nucleotide random sequence domain (N40). FIG. 1B. Selective amplification scheme for isolation of DNA that catalyzes the metal cofactor ($Co^{2+}$ or $Zn^{2+}$) dependent cleavage of an RNA phosphodiester.

FIG. 2. (SEQ ID NOS 13–23, respectively, in order of appearance) Sequence classes of the cloned Zn-DNA with clone numbers shown on the left, highly conserved sequences in bold, covariant nucleotides underlined, and 5'- and the 3'-primer binding sequences shown in italics.

FIG. 3. (SEQ ID NOS 24–42, respectively, in order of appearance) Sequence classes of the cloned Co-DNA with clone-numbers listed on the left and 5' and the 3' primer binding sequences in italics.

FIG. 4. (SEQ ID NOS 43–70, respectively, in order of appearance) Sequence alignment of the N40 region of the reselected Zn-DNAs with wild-type sequence listed on top, followed by reselected Zn-DNA sequences showing only point mutations. Shown on the left are clone-numbers and rate constants ($k_{obs}$) of several reselected Zn-DNA in 100 $\mu$M $Zn^{2+}$ are shown on the right.

Figure 5:
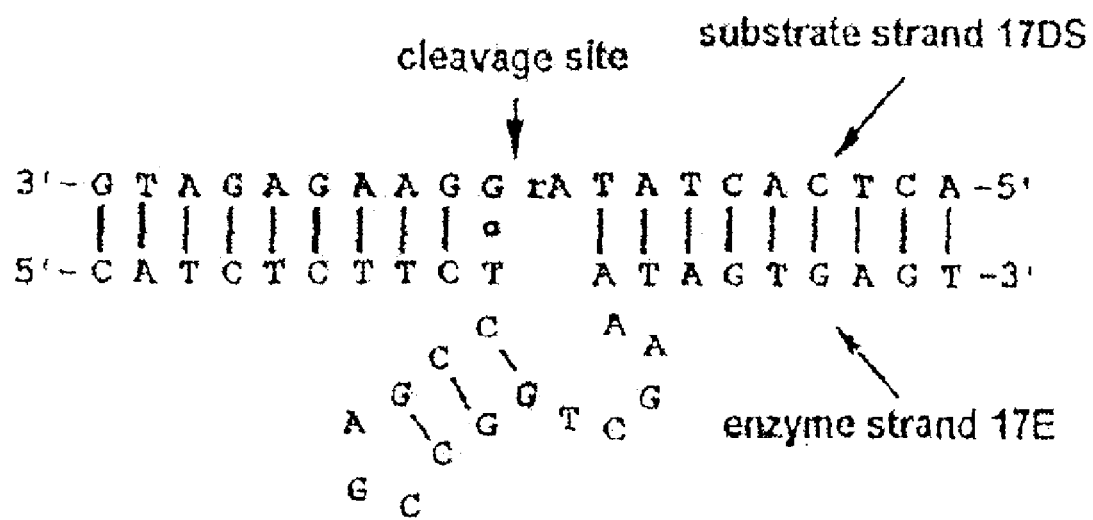

FIG. 5. (SEQ ID NOS 1 & 2) Proposed secondary structure of the Zn(II)-dependent trans-cleaving deoxyribozyme.

FIG. 6. Sequences and proposed secondary-structures of several RNA-cleaving deoxyribozymes. FIG. 6A (SEQ ID NOS 71 & 72) and FIG. 6B (SEQ ID NOS 73 & 74). The deoxyribozyme selected using $Mg^{2+}$ or $Pb^{2+}$ as cofactor (Breaker & Joyce, 1994, 1995). FIG. 6C (SEQ ID NOS 75 & 76) and FIG. 6D (SEQ ID NOS 77 & 78). The 10–23 and the 8–17 deoxyribozymes selected in $Mg^{2+}$ to cleave all-RNA substrate (Santoro & Joyce, 1997). FIG. 6E (SEQ ID NOS 79 & 80). A deoxyribozyme selected using L-histidine as cofactor. FIG. 6F (SEQ ID NOS 81 & 82). The 17E deoxyribozyme selected in $Zn^{2+}$. In each structure, the upper strand is the substrate and the lower strand is the enzyme. Arrows identify the site of RNA transesterification.

Figure 7A:
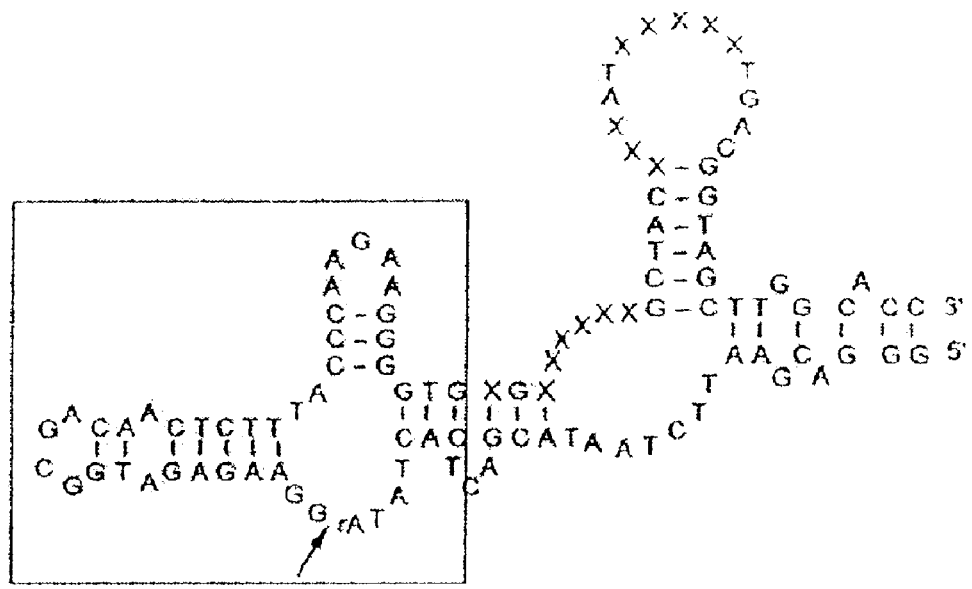
Figure 7B:
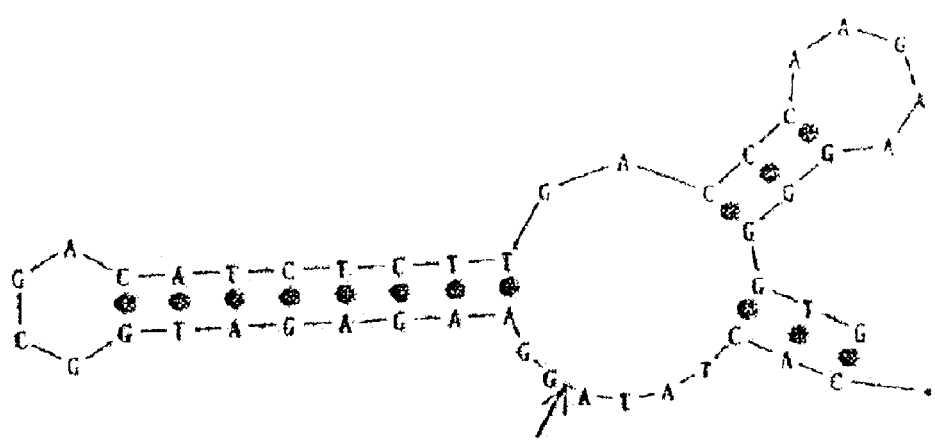

FIG. 7. Comparison of G3 deoxyribozyme with class II Co-DNA. FIG. 7A. (SEQ ID NO: 83) The predicted secondary structure of the G3 deoxyribozyme (Geyer & Sen, 1997) with X representing variable sequences. The boxed region was also found in class II Co-DNA. FIG. 7B. (SEQ ID NO: 84) The minimal structure motif of the class II Co-DNA predicted by mfold program with arrows indicating cleavage sites.

FIG. 8. Steady-state fluorescence spectra of the substrate (Rh-17DS) alone (I), after annealing to the deoxyribozyme (17E-Dy) (II), and 15 min after adding 500 nM Pb(OAc)$_2$ (III).

FIG. 9. $Pb^{2+}$ sensitive biosensor. FIG. 9A. Selectivity and sensitivity of biosensor for $Pb^{2+}$ at room temperature. FIG. 9B. Quantification of FIG. 9A. FIG. 9C. Time dependent curve illustrating fluorescence intensity increase for 500 nM divalent ions. Pb2+ curve is represented by the upper curve of dots. Other six metal ions, $Co^{2+}$, $Mg^{2+}$, $Zn^{2+}$, $Cd^{2+}$, $Mn^{2+}$, $Ni^{2+}$ are in the baseline level.

Figure 10A:
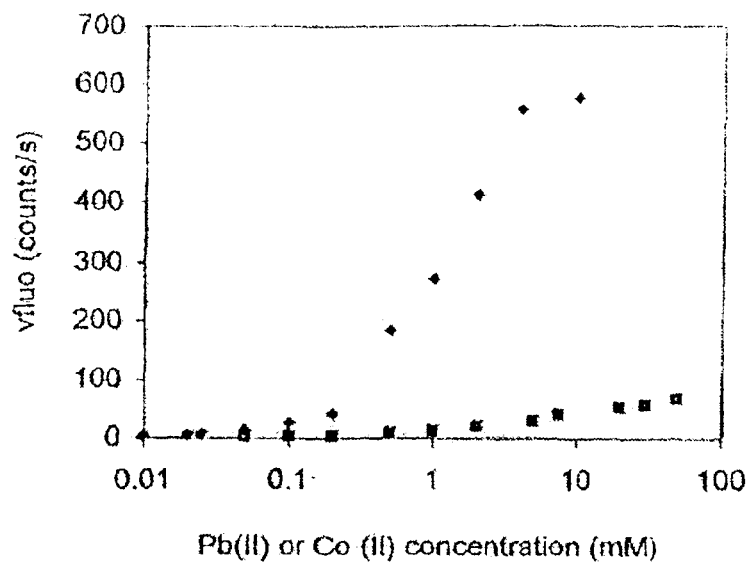
Figure 10B:
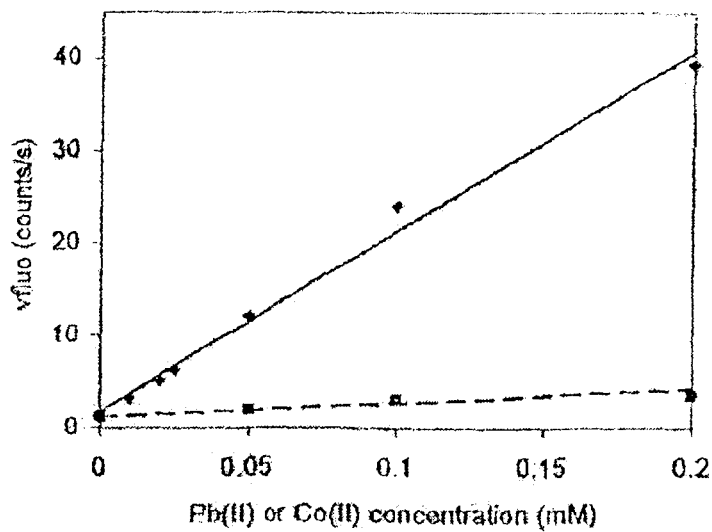

FIG. 10. Dependence of $v_{fluo}$ on the concentration of $Pb^{2+}$ or $Co^{2+}$. FIG. 10A. The initial rate ($v_{fluo}$) increased with the concentration of $Pb^{2+}$ (♦) and $Co^{2+}$ (■) over a range of three orders of magnitude. FIG. 10B. At low concentrations, $v_{fluo}$ increased linearly with $Pb^{2+}$ (♦) or $Co^{2+}$ (■) concentration.

Figure 11A:
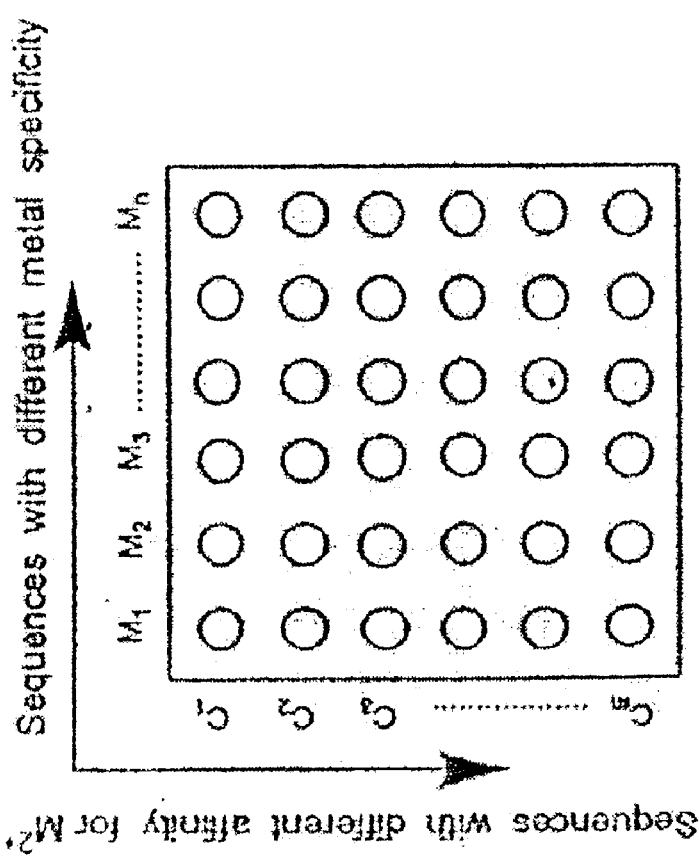
Figure 11B:
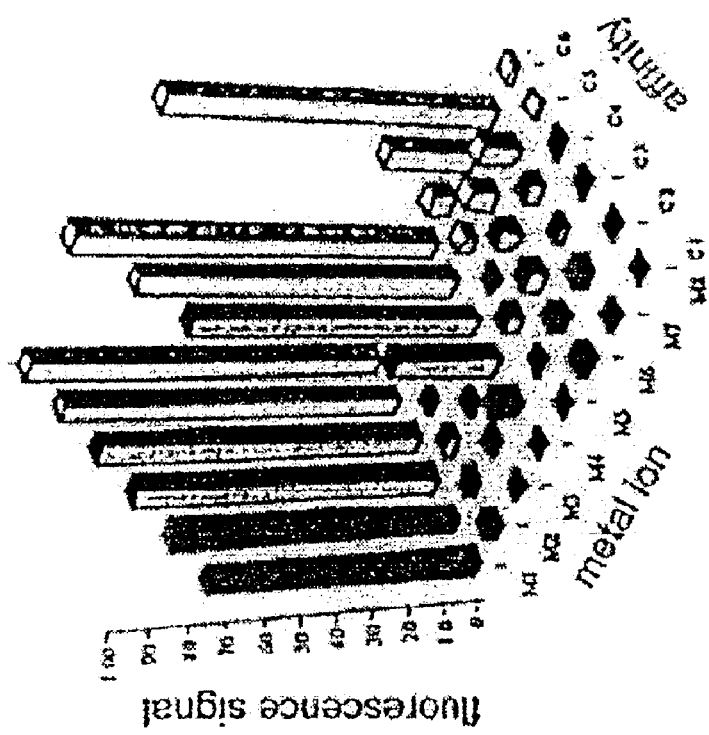

FIG. 11. DNA chips for ion sensing. FIG. 11A. The array of deoxyribozymes with different metal specificity and affinity on the DNA chip for metal ion sensing. FIG. 11B. (Hypothetical sample result) Quantitative and qualitative detection of metal ions using the metal ion-sensing deoxyribozyme chip with the z-axis representing fluorescence intensity change upon the exposure of the chip to the sample under examination.

Figure 12A:
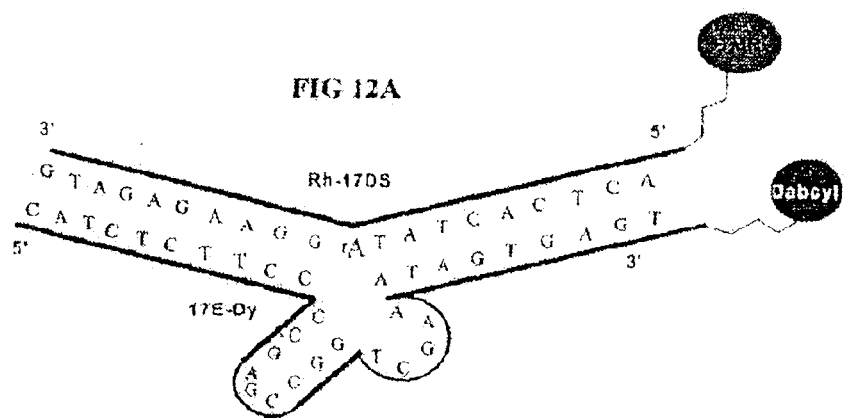
Figure 12B:
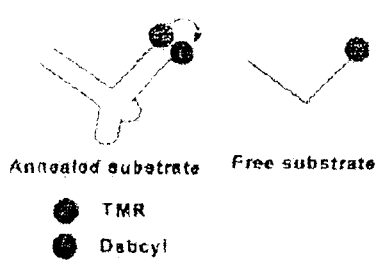
Figure 12C:
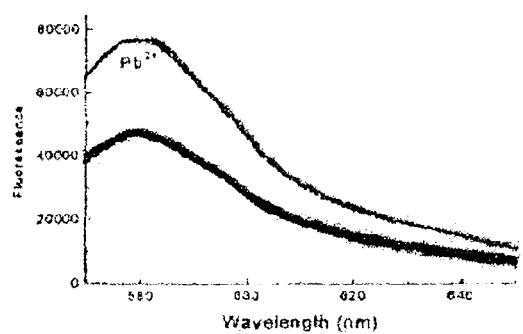

FIG. 12. Design of a biosensor of U.S. application Ser. No. 09/605,558, now U.S. Pat. No. 6,706,474. FIG. 12A The 3' end of the substrate is labeled with the fluorophore TAMRA and the 3' end of the enzyme is labeled with the quencher DABCYL $Pb^{2+}$ acts as a cofactor of this enzyme-substrate duplex, cleaving the substrate at the position of rA. FIG. 12B Representation of the biosensor system at room temperature, where the substrate and enzyme are poorly annealed and free substrate increases background fluorescence signal, making detection signal relatively weaker. FIG. 12C Room temperature fluorescence spectra for 1:1 substrate enzyme ratio in the absence of $Pb^{2+}$ (lower curve) and in the presence of $Pb^{2+}$ (upper curve). The fluorescence increase is only 60%.

Figure 13A:
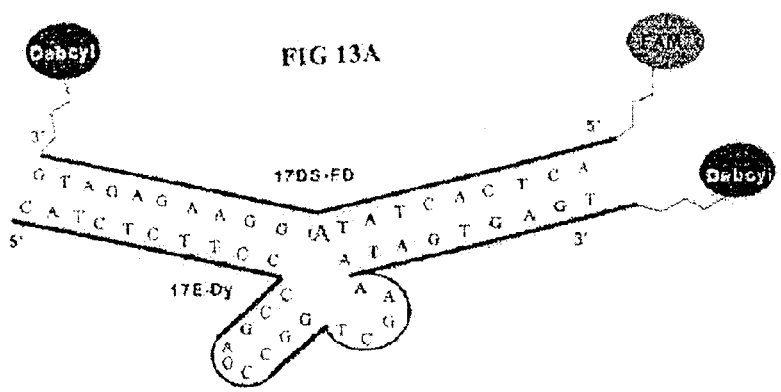
Figure 13B:
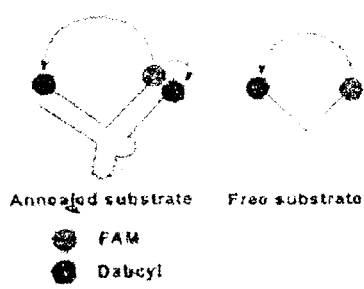
Figure 13C:
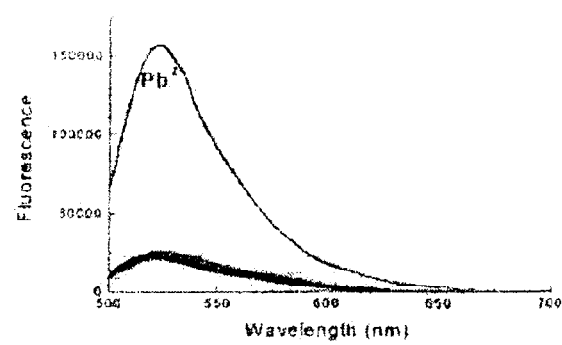

FIG. 13. Design of a biosensor with at least 2 quencher molecules and at least one fluorophore molecule. FIG. 13A The biosensor has a quencher molecule (DABCYL) located on the 3' end of both the substrate and enzyme and a fluorophore (FAM) on the 5' end of the enzyme. FIG. 13B Representation of the biosensor at room temperature, where regardless of hybridization between the enzyme and substrate, fluorescence is quenched in the absence of cleavage of the substrate. FIG. 13C Room temperature fluorescence spectra for 1:1 substrate enzyme ratio in the absence of $Pb^{2+}$ (lower curve) and in the presence of $Pb^{2+}$ (upper curve). The fluorescence is increased 660% over the background fluorescence signal, which is a more than 10 fold improvement over the biosensor design of FIG. 12.

Figure 14:

FIG. 14. Image comparison for the performance of the biosensor disclosed herein and the biosensor disclosed in U.S. application Ser. No. 09/605,558, now U.S. Pat. No. 6,706,474. (Images from a fluorescence image reader (Fuji)).

DETAILED DESCRIPTION

The present invention makes use of the discovery that including a second quencher can dramatically reduce background fluorescence signal in a biosensor system at room temperature, and thereby enhance sensitivity for ion detection.

U.S. application Ser. No. 09/605,558, now U.S. Pat. No. 6,706,474, describes a combination of a nucleic acid enzyme, including a quencher, and a nucleic acid substrate, including a fluorophore. This previous biosensor comprises a fluorophore and quencher arranged in proximity such that prior to cleavage the fluorophore and quencher are proximal to one another and fluorescence intensity is decreased by the quencher. Upon binding of a specifically recognized ion, for example $Pb^{2+}$, cleavage occurs and the fluorophore and quencher are separated, leading to an increase in fluorescence intensity, which may then be detected. However, at room temperature (around 23° C.), due to the relatively low hybridization temperature of the enzyme-substrate duplex (around 35° C.), a fraction of the duplex melts, resulting in free substrate labeled with a fluorophore, which leads to a high level of background fluorescence signal. To overcome this problem, application Ser. No. 09/605,558, now U.S. Pat. No. 6,706,474 describes using the enzyme-substrate duplex at low temperatures, around 4° C., to promote annealing of the enzyme and substrate. At 4° C., this enzyme-substrate duplex yields a 400% increase in fluorescence signal intensity, compared to only 60% increase in signal intensity at room temperature (FIGS. 12C, 13C and 14). This significant decrease in signal intensity greatly detracts from the sensitivity and interpretability of the results of such a test.

One method for overcoming increased background signal due to increased free substrate at higher temperatures would be to increase the hybridization strength of the recognition arms, thereby making the substrate-enzyme duplex more stable. While this method would decrease background fluorescence signal at higher temperatures, it would also greatly increase the reaction time due to slow release of the cleaved substrate recognition arms. The present invention avoids both problems by adding a quencher to the substrate on the end opposite the fluorophore. This design successfully prevents significant levels of background fluorescence because when the substrate is poorly annealed to the enzyme it forms a random coil so that the end-to-end distance is much shorter than in the fully stretched, annealed state, resulting in significant energy transfer from fluorophore to quencher, thereby significantly decreasing any detectable background fluorescence signals.

The present invention has much less background fluorescence. For example, in one embodiment, selectivity for $Pb^{2+}$ was increased 10 fold at room temperature over the $Pb^{2+}$ sensitive biosensor of U.S. application Ser. No. 09/605,558, now U.S. Pat. No. 6,706,474, which itself has selectivity for $Pb^{2+}$ more than 80 fold over other divalent metal ions with high sensitivity (660% signal increase over background fluorescence signal of the new biosensor compared to 60% signal increase over background of the biosensor of U.S. application Ser. No. 09/605,558, now U.S. Pat. No. 6,706, 474, at room temperature) (FIG. 14). Such selectivity and sensitivity provide for qualitative and quantitative detection of ions over a concentration range of several orders of magnitude. The new biosensor also provides easily interpretable results, by lowering background fluorescence signals to almost zero. The fluorescence domain of this biosensor may be decoupled from the ion-recognition/catalysis domain, and therefore the sensitivity and signal over background ratio of this system may be manipulated by a careful choice of fluorophores and by performing in vitro selection of ion-binding domains to not only keep sequences reactive with the ion of choice, but also remove sequences that also respond to other ions.

The present invention provides a simple, rapid, inexpensive, selective and sensitive method for detecting the presence of an ion, with background fluorescence signal near zero and effective at any temperature, and is an important and useful tool in preventing or at least lowering health and environmental risks associated with environmental contaminants.

DNA is stable, inexpensive and easily adaptable to optical fiber and chip technology for device manufacture. The attachment of DNA enzymes to optical fibers or chips allows regeneration of the sensors by washing away the cleavage products and adding new substrates. Finally, sequences specific for other ions and with various detection ranges may be isolated by varying the selection conditions, providing for a highly sensitive and selective fluorosensor system.

Nucleic Acid Enzymes

A growing number of nucleic acid enzymes have been discovered or developed showing a great diversity in catalytic activity (Table 1 and Table 2). Many, if not all, of the enzymes are dependent on one or more ion cofactors. In vitro selection may be used to "enhance" selectivity and sensitivity for a particular ion. Such enzymes find particular utility in the compositions and methods of the present invention. For example, nucleic acid enzymes that catalyze molecular association (ligation, phosphorylation, and amide bond formation) or dissociation (cleavage or transfer) are particularly useful.

In preferred embodiments, a nucleic acid enzyme that catalyzes the cleavage of a nucleic acid in the presence of an ion is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available, e.g., from Biosearch, Inc. (Bedford, Mass.).

Ribozymes that may be used in the present invention include, but are not limited to, group I and group II introns, the RNA component of the bacterial ribonuclease P, hammerhead, hairpin, hepatitis delta virus and Neurospora VS ribozymes. Also included are in vitro selected ribozymes, such as those isolated by Tang and Breaker (2000).

One limitation of using a ribozyme is that they tend to be less stable than deoxyribozymes. Thus, in preferred embodiments, the nucleic acid enzyme is a deoxyribozyme. Preferred deoxyribozymes include those shown in FIGS. 6A–6F and deoxyribozymes with extended chemical functionality (Santoro et al., 2000).

TABLE 1

Reactions catalyzed by ribozymes that were isolated from in vitro selection experiments.

| Reaction | $k_{cat}$ (min$^{-1}$) | $K_m$ ($\mu$M) | $k_{cat}/k_{uncat}$[a] | Reference |
|---|---|---|---|---|
| Phosphoester centers | | | | |
| Cleavage | 0.1 | 0.03 | $10^5$ | Vaish, 1998 |
| Transfer | 0.3 | 0.02 | $10^{13}$ | Tsang, 1996 |
| Ligation | 100 | 9 | $10^9$ | Ekland, 1995 |
| Phosphorylation | 0.3 | 40 | $>10^5$ | Lorsch, 1994 |
| Mononucleotide polymerization | 0.3 | 5000 | $>10^7$ | Ekland, 1996 |
| Carbon centers | | | | |
| Aminoacylation | 1 | 9000 | $10^6$ | Illangasekare, 1997 |
| Aminoacyl ester hydrolysis | 0.02 | 0.5 | 10 | Piccirilli, 1992 |
| Aminoacyl transfer | 0.2 | 0.05 | $10^3$ | Lohse, 1996 |
| N-alkylation | 0.6 | 1000 | $10^7$ | Wilson, 1995 |
| S-alkylation | $4 \times 10^{-3}$ | 370 | $10^3$ | Wecker, 1996 |
| Amide bond cleavage | $1 \times 10^{-5}$ | | $10^2$ | Dai, 1995 |
| Amide bond formation | 0.04 | 2 | $10^5$ | Wiegand, 1997 |
| Peptide bond formation | 0.05 | 200 | $10^6$ | Zhang, 1997 |
| Diels-Alder cycloaddition | $>0.1$ | $>500$ | $10^3$ | Tarasow, 1997 |
| Others | | | | |
| Biphenyl isomerization | $3 \times 10^{-5}$ | 500 | $10^2$ | Prudent, 1994 |
| Porphyrin metallation | 0.9 | 10 | $10^3$ | Conn, 1996 |

[a]Reactions catalyzed by ribozymes that were isolated from in vitro selection experiments. kcat/kuncat is the rate enhancement over uncatalyzed reaction.

TABLE 2

Deoxyribozymes isolated through in vitro selection.

| Reaction | Cofactor | $k_{max}$(min$^{-1}$)[a] | $k_{cat}/k_{uncat}$ | Reference |
|---|---|---|---|---|
| RNA transesterification | Pb$^{2+}$ | 1 | $10^5$ | Breaker, 1994 |
| | Mg$^{2+}$ | 0.01 | $10^5$ | Breaker, 1995 |
| | Ca$^{2+}$ | 0.08 | $10^5$ | Faulhammer, 1997 |
| | Mg$^{2+}$ | 10 | $>10^5$ | Santoro, 1997 |
| | None | 0.01 | $10^8$ | Geyer, 1997 |
| | L-histidine | 0.2 | $10^6$ | Roth, 1998 |
| | Zn$^{2+}$ | ~40 | $>10^5$ | Li, J., 2000 |
| DNA cleavage | Cu$^{2+}$ | 0.2 | $>10^6$ | Carmi, 1996 |
| DNA ligation | Cu$^{2+}$ or Zn$^{2+}$ | 0.07 | $10^5$ | Cuenod, 1995 |
| DNA phosphorylation | Ca$^{2+}$ | 0.01 | $10^9$ | Li, Y., 1999 |
| 5',5'-pyrophophate formation | Cu$^{2+}$ | $5 \times 10^{-1}$ | $>10^{10}$ | Li, Y., 2000 |
| Porphyrin methalation | None | 1.3 | $10^3$ | Li, Y., 1996 |

[a]$k_{max}$ is the maximal rate constant obtained under optimized conditions.

An advantage of ribozymes and deoxyribozymes is that they may be produced and reproduced using biological enzymes and appropriate templates. However, the present invention is not limited to ribozymes and deoxyribozymes. Nucleic acid enzymes that are produced by chemical oligo-synthesis methods are also included. Thus, nucleic acids including nucleotides containing modified bases, phosphate, or sugars may be used in the compositions and methods of the present invention. Modified bases are well known in the art and include inosine, nebularine, 2-aminopurine riboside, N$^7$-denzaadenosine, and O$^6$-methylguanosine (Earnshaw &

Gait, 1998). Modified sugars and phosphates are also well known and include 2'-deoxynucleoside, abasic, propyl, phosphorothioate, and 2'-O-allyl nucleoside (Eamshaw & Gait, 1998). DNA/RNA hybrids and PNAs may be used in the compositions and methods of the present invention. The stability of PNAs and relative resistance to cellular nucleases make PNA enzymes amenable to in vivo applications.

In certain embodiments, the substrate for the nucleic acid enzyme and the enzyme itself are contained in the same nucleic acid strand. Such enzymes are cis-acting enzymes. Examples include the $Zn^{2+}$-dependent deoxyribozymes (Zn-DNA) created in Example 1 (FIG. 1A and FIG. 2).

In preferred embodiments, the nucleic acid enzyme cleaves a nucleic acid strand that is separate from the strand comprising the enzyme (trans-acting). One advantage of utilizing trans-activity is that, after cleavage, the product is removed and additional substrate may be cleaved by the enzymatic strand. A preferred nucleic acid enzyme is 5'-CATCTCTTCTCCGAGCCGGTCGAAATAGTGAGT-3' (17E; FIG. 5; SEQ ID NO:1). The corresponding preferred substrate to 17E is 5'-ACTCACTATrAGGAAGAGATG-3 (17DS; FIG. 5; SEQ ID NO: 2), where rA denotes a single ribonucleotide.

It may be beneficial to use directed mutation to change one or more properties of a nucleic acid enzyme or its substrate. Using 17E and 17DS-FD as an example, one may wish to alter the avidity of the two arms of the hybridized enzyme and substrate. The "arms" are those areas displaying Watson-Crick basepairing in FIG. 5. To alter avidity, one may increase or decrease the length of the arms. Increasing the length of the arms increases the number of Watson-Crick bonds, thus increasing the avidity. The opposite is true for decreasing the length of the arms. Decreasing the avidity of the arms facilitates the removal of substrate from the enzyme, thus allowing faster enzymatic turnover.

Another method of decreasing avidity includes creating mismatches between the enzyme and the substrate. Alternatively, the G-C content of the arms may be altered. Of course, the effect of any directed change should be monitored to ensure that the enzyme retains its desired activity, including ion sensitivity and selectivity. In light of the present disclosure, one of skill in the art would understand how to monitor for a desired enzymatic activity. For example, to ensure that the mutated enzyme maintained sensitivity and selectivity for $Pb^{2+}$, one would test to determine if the mutated enzyme remained reactive in the presence of lead (sensitivity) and maintained its lower level of activity in the presence of other ions (selectivity).

The nucleic acid enzyme is sensitive and selective for a single ion. The ion may be any anion, for example, arsenate ($AsO_4^{3-}$), or cation. The ion may be monovalent, divalent, trivalent, or polyvalent. Examples of monovalent cations include $K^+$, $Na^+$, $Li^+$, $Tl^+$, $NH_4^+$ and $Ag^+$. Examples of divalent cations include $Mg^{2+}$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Hg^{2+}$, $Pt^{2+}$, $Ra^{2+}$, $Ba^{2+}$, $UO_2^{2+}$ and $Sr^{2+}$. Examples of trivalent cations include $Co^{3+}$, $Cr^{3+}$, and lanthanide ions ($Ln^{3+}$). Polyvalent cations include $Ce^{4+}$, $Cr^{6+}$, spermine, and spermidine. The ion detected by the biosensor also includes ions having a metal in a variety of oxidation states. Examples include K(I), Na(I), Li(I), Tl(I), Ag(I), Hg(I), Mg(II), Ca(II), Mn(II), Co(II), Ni(II), Zn(II), Cd(II), Pb(II), Hg(II), Pt(II), Ra(II), Ba(II), Sr(II), Co(III), Cr(III), Ln(III), Ce(IV), Cr(VI) and U(VI).

The biosensors of the present invention may be used to monitor contaminants in the environment; in such a case preferred ions are those that are toxic to living organisms, e.g., $Ag^+$, $Pb^{2+}$ and $Hg^{2+}$.

Often the nucleic acid enzymes that have activity with one ion also have at least some activity with one or more other ions. Such multi-sensitive enzymes may still be used in the compositions and methods of the present invention. However, it should be understood that use of a multi-sensitive enzyme may lead to uncertainty as to which of the ions is present. In such cases, measuring the rate of enzymatic activity, using serial dilutions, or using an array of nucleic acid enzymes may be helpful in deciphering which ion is present.

In Vitro Selection of Nucleic Acid Enzymes

Many nucleic acid enzymes that are dependent on ions, particularly metal ions, for activity are known in the art (Breaker & Joyce, 1994; Pan & Uhlenbeck, 1992; Cuenoud & Szostak, 1995; Carmi et al., 1996; Li et al., 2000; Santoro et al., 2000). In light of the present disclosure, one of skill in the art would understand how to utilize a known nucleic acid enzyme in the methods and biosensors of the present invention. Furthermore, the present invention may include a nucleic acid enzyme created by in vitro selection. Methods of in vitro selection of nucleic acid enzymes are known in the art and described herein.

In vitro selection is a technique in which RNA or DNA molecules with certain functions are isolated from a large number of sequence variants through multiple cycles of selection and amplification (Joyce, 1994; Chapman et al., 1994). The concept of in vitro selection of catalytic RNA molecules was first introduced in the late 1980's. Since then, it has been widely applied to obtain ribozymes with maximized activities or novel catalytic abilities, and to identify oligonucleotides (called aptamers) that bind to certain proteins or small molecules with high affinity. The process for aptamers selection is sometimes referred as systematic evolution of ligands by exponential enrichment (SELEX)(Tuerk & Gold, 1990).

The first catalytic DNA (deoxyribozyme) was isolated by Breaker and Joyce in 1994 through in vitro selection. This deoxyribozyme is able to catalyze phosphodiester cleavage reaction in the presence of $Pb^{2+}$. Unlike RNA-based catalysts, DNA molecules with catalytic functions have not been encountered in nature, where DNA exists primarily as base-paired duplex and serves mainly as the carrier of genetic information. The identification of DNA molecules with catalytic functions further demonstrated the power of in vitro selection.

In vitro selection is typically initiated with a large collection of randomized sequences. A typical DNA or RNA library for selection contains $10^{13}$–$10^{16}$ sequence variants. The construction of a completely randomized pool is accomplished by chemical synthesis of a set of degenerated oligonucleotides using standard phosphoramidite chemistry. The 3'-phosphoramidite compounds of four nucleosides (A, C, G, and T) are premixed before being supplied to an automated DNA synthesizer to produce oligonucleotides. By controlling the ratio of four phosphoroamidites, the identity at each nucleotide position can be either completely random, i.e. with equal chance for each base, or biased toward a single base. Other strategies for creating a randomized DNA library include applying mutagenic polymerase chain reaction (PCR) and template-directed mutagenesis (Tsang and Joyce, 1996; Cadwell and Joyce, 1992, 1994). For the purpose of in vitro selection of functional RNA molecules, the randomized DNA library is converted to an RNA library through in vitro transcription.

In vitro selection takes advantage of a unique property of RNA and DNA, i.e., the same molecule can possess both genotype (coding information) and phenotype (encoded function). The DNA or RNA molecules in the randomized library are screened simultaneously. Those sequences that exhibit a desired function (phenotype) are separated from the inactive molecules. Usually the separation is performed through affinity column chromatography, being linked to or released from a solid support, gel electrophoresis separation, or selective amplification of a tagged reaction intermediate. The genotype of the active molecules are then copied and amplified, normally through polymerase chain reaction (PCR) for DNA or isothermal amplification reaction for RNA (Guatelli et al., 1990). Mutations can be performed with mutagenic PCR to reintroduce diversity to the evolving system. These three steps-selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA far beyond what has been found in nature. The selected ribozymes are capable of catalyzing a wide range of reactions at both phosphate and non-phosphate centers (Table 1). The reactions that are catalyzed by deoxyribozymes are less diverse, compared with the ribozymes (Table 2). However, the catalytic rate ($k_{cat}$) of most deoxyribozymes is comparable to that of the ribozymes catalyzing the same reaction. In certain cases, the catalytic efficiency ($k_{cat}/K_m$) of nucleic acid enzymes even exceeds that of the protein enzymes.

Figure 6A:
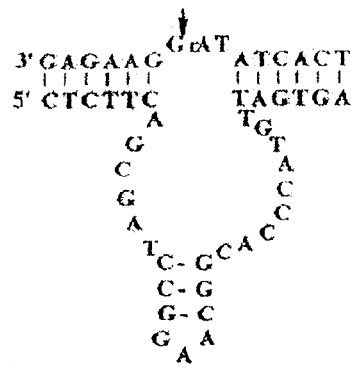
Figure 6B:
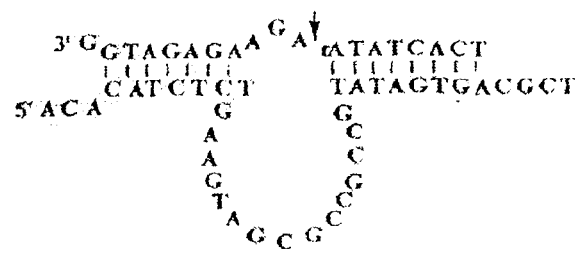
Figure 6C:
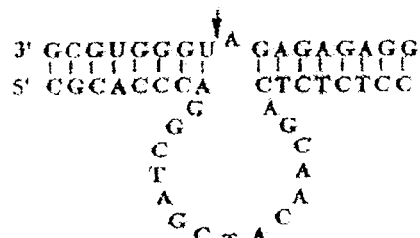
Figure 6D:
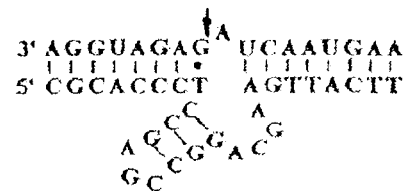
Figure 6E:
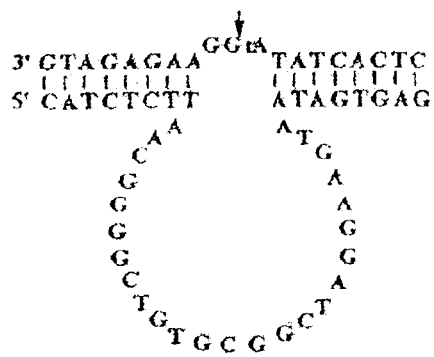
Figure 6F:
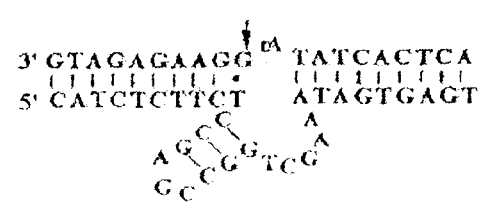

In vitro selection can be used to change the ion specificity or binding affinity of existing ribozymes, or to obtain nucleic acid enzymes specific for desired ions. For example, in vitro-selected variants of the group I intron (Lehman & Joyce, 1993) and the RNase P ribozyme (Frank & Pace, 1997) have greatly improved activity in $Ca^{2+}$, which is not an active metal ion cofactor for native ribozymes. The $Mg^{2+}$ concentration required for optimal hammerhead ribozyme activity has been lowered using in vitro selection to improve the enzyme performance under physiological conditions (Conaty et al., 1999; Zillman et al., 1997). Breaker and Joyce have isolated several RNA-cleaving deoxyribozymes using $Mg^{2+}$, $Mn^{2+}$, $Zn^{2+}$, or $Pb^{2+}$ as the cofactor (Breaker & Joyce, 1994, 1995). Only the sequence and structure of the $Pb^{2+}$-dependent and the $Mg^{2+}$-dependent deoxyribozymes were reported (FIGS. 6A and 6B). Other examples of metal-specific RNA/DNA enzymes obtained through in vitro selection include a $Pb^{2+}$-specific RNA-cleaving ribozyme (called leadzyme)(Pan & Uhlenbeck, 1992), a $Cu^{2+}$-specific DNA-cleaving deoxyribozyme (Carmi et al., 1996), and a DNA ligase active in $Zn^{2+}$ and $Cu^{2+}$ (Cuonod & Szostak, 1995).

Often nucleic acid enzymes developed for a specific metal ion by in vitro selection will have activity in the presence of other metal ions. For example, 17E deoxyribozyme was developed by in vitro selection for activity in the presence of $Zn^{2+}$. Surprisingly, the enzyme showed greater activity in the presence of $Pb^{2+}$ than $Zn^{2+}$. Thus, although produced in a process looking for $Zn^{2+}$-related activity, 17E may be used as a sensitive and selective sensor of $Pb^{2+}$.

To produce nucleic acid enzymes with greater selectivity, a negative selection step may be included in the process. For Example, $Pb^{2+}$-specific deoxyribozymes may be isolated using a similar selection scheme as for the selection of $Co^{2+}$- and $Zn^{2+}$-dependent DNA enzymes described in Example 1. In order to obtain deoxyribozymes with high specificity for $Pb^{2+}$, negative-selections may be carried out in addition to the positive selections in the presence of $Pb^{2+}$.

For negative selection, the DNA pool is selected against a "metal soup", which contains various divalent metal ions (e.g. $Mg^{2+}$, $Ca^{2+}$, $Mn^{2+}$, $Zn^{2+}$, $Cd^{2+}$, $Co^{2+}$, $Cu^{2+}$, etc.). Those sequences that undergo self-cleavage in the presence of divalent metal ions other than $Pb^{2+}$ are then washed off the column. The remaining sequences are further selected with $Pb^{2+}$ as the cofactor. $Pb^{2+}$-dependent deoxyribozymes with different affinities for $Pb^{2+}$ can be obtained by controlling the reaction stringency ($Pb^{2+}$ concentration).

Fluorophores and Quenchers

Any chemical reaction that leads to a fluorescent or chemiluminescent signal may be used in the compositions and methods of the present invention. In preferred embodiments, fluorophores are used to measure enzymatic activity and, thus, detect the presence of a particular ion. Essentially any fluorophore may be used, including BODIPY, fluoroscein, fluoroscein substitutes (Alexa Fluor dye, Oregon green dye), long wavelength dyes, and UV-excited fluorophores. These and additional fluorophores are listed in *Fluorescent and Luminescent Probes for Biological Activity. A Practical Guide to Technology for Quantitative Real-Time Analysis*, Second Ed. W. T. Mason, ed. Academic Press (1999) (incorporated herein by reference). In preferred embodiments, the fluorophore is 6-carboxyfluorescein (FAM). FAM has an excitation range of 460–500 nm.

A quencher is a molecule that absorbs the energy of the excited fluorophore. Close proximity of a fluorophore and a quencher allow for the energy to be transferred from the fluorophore to the quencher. By absorbing this energy, the quencher prevents the fluorophore from releasing the energy in the form of a photon, thereby preventing fluorescence.

Quenchers may be categorized as non-fluorescent and fluorescent quenchers. Non-fluorescent quenchers are capable of quenching the fluorescence of a wide variety of fluorophores. Generally, non-fluorescent quenchers absorb energy from the fluorophore and release the energy as heat. Examples of non-fluorescent quenchers include 4-(4'-dimethylaminophenylazo)benzoic acid) (DABCYL), QSY-7, and QSY-33.

Fluorescent quenchers tend to be specific to fluorophores that emit at a specific wavelength range. Fluorescent quenchers often involve fluorescence resonance energy transfer (FRET). In many instances the fluorescent quencher molecule is also a fluorophore. In such cases, close proximity of the fluorophore and fluorescent quencher is indicated by a decrease in fluorescence of the "fluorophore" and an increase in fluorescence of the fluorescent quencher. Commonly used fluorescent fluorophore pairs (fluorophore/fluorescent quencher) include fluorescein/tetramethylrhodamine, IAEDANS/fluorescein, fluorescein/fluorescein, and BODIPY FL/BODIPY FL.

When choosing a fluorophore, a quencher, or where to position these molecules, it is important to consider, and preferably to test, the effect of the fluorophore or quencher on the enzymatic activity of the nucleic acid enzyme. Also, it is preferable that the fluorophore display a high quantum yield and energy transfer efficiency. Long-wavelength (excitation and emission) fluorophores are preferred because of less interference from other absorbing species. The fluorophore should also be less sensitive to pH change or to non-specific quenching by metal ions or other species.

Methods and devices for detecting fluorescence are well developed. Essentially any instrument or method for detecting fluorescent emissions may be used. For example, WO 99/27351 (incorporated herein in its entirety) describes a monolithic bioelectrical device comprising a bioreporter and an optical application specific integrated circuit (OASIC). The device allows remote sampling for the presence of substances in solution.

Furthermore, the fluorescence may be measured by a number of different modes. Examples include fluorescence intensity, lifetime, and anisotropy in either steady state or kinetic rate change modes (Lakowicz, 1999).

Sometimes other factors in a solution such as pH, salt concentration or ionic strength, or viscosity will have an effect on fluorescence, and may even affect the hybridization of the substrate and enzyme. Therefore, in preferred methods, controls are run to determine if the solution itself, regardless of enzymatic activity, is altering the fluorescence. Such controls include the use of non-cleavable substrates and or substrate without the presence of enzyme.

Biosensors

A biosensor is a device which is capable of detecting target analytes by utilizing biological reactions. The biosensor of the present invention is quite different from a bioaffinity sensor, which relies on specific binding and recognition events of target DNA sequences, because a biosensor takes advantage of its own catalytic activities, caused by a target analyte or ion.

For example, described herein are biosensors which are nucleic acid enzymes that are dependent on the presence of a specific ion for activity. Using fluorophores or fluorophore/quencher labeling, it is possible to measure enzymatic activity, even in real time. These qualities make the compositions of the present invention excellent for use in biosensors, which are useful for detecting the presence of a target ion in the presence of other ions.

A key to biosensor detection methods is to minimize background fluorescence signals by maintaining the fluorophore and quenchers in close proximity in the absence of cleavage. Therefore the fluorophore could be linked essentially anywhere on the substrate and quenchers could be linked essentially anywhere on the substrate and enzyme, as long as the fluorophore is in close proximity to at least one of the quenchers prior to cleavage. By close proximity, it is meant that they are situated such that the quencher is able to function (i.e., where efficiency of energy transfer between the quencher and the fluorophore is 50% or more), and preferably are less than a distance of 20 nucleic acid bases or 70 angstroms. For example, a fluorophore may be linked to one end of the substrate in the substrate-enzyme duplex, while a quencher is linked to the opposite end of the substrate and a second quencher is linked to the end of the enzyme which hybridizes with the fluorophore labeled end of the substrate. (FIG. 13A) This configuration provides the advantage of continually keeping the fluorophore, in the absence of cleavage, proximal to a quencher, regardless of hybridization of the substrate-enzyme duplex, thereby eliminating nearly all background fluorescence signals. In the presence of the target ion the substrate is cleaved and the product disassociates from the enzyme. Dissociation of the product removes the fluorophore from the vicinity of the quenchers, leading to an increase in fluorescence (FIG. 8).

It should be appreciated that the design of the present invention relies on the polymer end-to-end distance distribution. Therefore it may not be general for long strand polymers. However, in such long strand polymers, the quencher may be placed in the middle of the polymer or any other appropriate position, thereby eliminating the problem of being too distant.

It should also be appreciated that FRET can be used for sensing, detecting, identifying or quantifying a target ion in the present invention by using a fluorescent quencher instead of a non-fluorescent quencher.

In light of the present disclosure, one of ordinary skill in the art would know how to modify the nucleic acid biosensors to include nucleic acid enzymes. For example, a biosensor of the present invention may comprise a nucleic acid enzyme labeled with a fluorescent quencher, a substrate labeled with a fluorophore and a second fluorescent quencher, and a device to detect fluorescence such as a fluorescence microscope or a fluorometer. In a method using this embodiment, the enzyme and substrate are contacted with a sample suspected of containing an ion to which the enzyme is sensitive. Fluorescence is measured and compared to a control wherein the ion is absent. Change in fluorescence is indicative of the presence of the ion.

Of course, many variants of even this simple embodiment are included within the scope of the invention. Such variants include placing the enzyme, substrate, and sample in the well of a microtiter plate and measuring fluorescence with a microtiter plate reader. In another variation, the enzyme is attached to a solid support. When the enzyme is attached to a solid support, it is preferable that a linker is used. An exemplary linking system is biotin/streptavidin. For example, the biotin molecule may be linked to the enzyme and a plate may be coated with streptavidin. When linking an enzyme to a solid support, it is important to determine the effect of linkage on the enzymatic activity of the enzyme.

In an alternative embodiment, the solid support may be a bead and fluorescence measured using a flow cytometer. In embodiments having the enzyme attached to a solid support, the biosensor may be reusable. Old substrate and sample is removed, leaving the enzyme in place. New substrate and sample may then be added.

In another embodiment, the nucleic acid enzyme may be used in conjunction with fiber-optics (Lee & Walt, 2000). The nucleic acid enzyme may be immobilized on the surface of silica microspheres and distributed in microwells on the distal tip of an imaging fiber. The imaging fiber may then be coupled to a epifluorescence microscope system.

In certain embodiments, the biosensor will comprise an array of nucleic acid enzymes. The arrays of the present invention provide for the simultaneous screening of a variety of ions by nucleic acid enzymes. The array may contain as little as 2 or as many as 10,000 different nucleic acid enzymes. Of course, any integer in between may be used. Preferably, each individual nucleic acid enzyme has a measurable difference in specificity or affinity for at least one ion compared to at least one other nucleic acid enzyme within the array.

In preferred embodiments, the array is a high-density array like those used in DNA-chip technologies. Methods of forming high density arrays of nucleic acids with a minimal number of synthetic steps are known (U.S. Pat. No. 6,040, 138). The nucleic acid array can be synthesized on a solid support by a variety of methods, including light-directed chemical coupling, and mechanically directed coupling (U.S. Pat. No. 5,143,854; WO 90/15070; WO 92/10092; WO 93/09668). Using this approach, one heterogenous array of polymers is converted, through simultaneous coupling at a number of reaction sites, into a different heterogenous array.

The light-directed combinatorial synthesis of nucleic acid arrays on a glass surface uses automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different nucleic acid analogues at different locations on the array is determined by the pattern of illumination during synthesis and the order of addition of coupling reagents.

In the event that a PNA is used in the procedure, it is generally inappropriate to use phosphoramidite chemistry to perform the synthetic steps, since the monomers do not attach to one another via a phosphate linkage. Instead, peptide synthetic methods are substituted (U.S. Pat. No. 5,143,854).

In addition to the foregoing, additional methods which can be used to generate an array of nucleic acids on a single solid support are known (For example, WO 93/09668). In these methods, reagents are delivered to the solid support by either (1) flowing within a channel defined on predefined regions or (2) "spotting" on predefined regions. However, other approaches, as well as combinations of spotting and flowing, may be employed. In each instance, certain activated regions of the solid support are mechanically separated from other regions when the monomer solutions are delivered to the various reaction sites.

A typical "flow channel" method applied to the nucleic acid enzyme arrays of the present invention can generally be described as follows. Diverse nucleic acid sequences are synthesized at selected regions of a solid support by forming flow channels on a surface of the solid support through which appropriate reagents flow or in which appropriate reagents are placed. For example, assume a monomer "A" is to be bound to the solid support in a first group of selected regions. If necessary, all or part of the surface of the solid support in all or a part of the selected regions is activated for binding by, for example, flowing appropriate reagents through all or some of the channels, or by washing the entire solid support with appropriate reagents. After placement of a channel block on the surface of the solid support, a reagent having the monomer A flows through or is placed in all or some of the channel(s). The channels provide fluid contact to the first selected regions, thereby binding the monomer A on the solid support directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the solid support; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the solid support at this stage of processing will be, for example, A, B, and AB. The process is repeated to form a vast array of nucleic acid enzymes of desired length and sequence at known locations on the solid support.

After the solid support is activated, monomer A can be flowed through some of the channels, monomer B can be flowed through other channels, a monomer C can be flowed through still other channels, etc. In this manner, many or all of the reaction regions are reacted with a monomer before the channel block must be moved or the solid support must be washed and/or reactivated. By making use of many or all of the available reaction regions simultaneously, the number of washing and activation steps can be minimized.

There are alternative methods of forming channels or otherwise protecting a portion of the surface of the solid support. For example, according to some embodiments, a protective coating such as a hydrophilic or hydrophobic coating (depending upon the nature of the solvent) is utilized over portions of the solid support to be protected, sometimes in combination with materials that facilitate wetting by the reactant solution in other regions. In this manner, the flowing solutions are further prevented from passing outside of their designated flow paths.

The "spotting" methods of preparing nucleic acid arrays can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire solid support surface can be sprayed or otherwise coated with a solution. In preferred embodiments, a dispenser moves from region to region, depositing only as much monomer as necessary at each stop. Typical dispensers include a micropipette to deliver the monomer solution to the solid support and a robotic system to control the position of the micropipette with respect to the solid support. In other embodiments, the dispenser includes a series of tubes, a manifold, an array of pipettes, or the like so that various reagents can be delivered to the reaction regions simultaneously.

The biosensors of the array may be selective for a single type of ion or each biosensor may be selective for a different type of ion. The substrates for the nucleic acid enzymes of the array may be labeled with a single fluorophore or with different fluorophores. For example, a biosensor, selective for the presence of $Pb^{2+}$, may be designed to emit a certain fluorescence, such as FAM, in the presence of $Pb^{2+}$. An array may be covered with this biosensor. Another example would include an array comprising several biosensors, where one is selective for the presence $Zn^{2+}$, another is selective for the presence of $Pb^{2+}$, and a third biosensor is selective for the presence of $Co^{2+}$. Each of these three biosensors of the array may be designed to emit a single type of fluorescence, such as FAM, in the presence of each respective specific ion or each of these three biosensors may be designed to emit a different type of fluorescence in the presence of each respective specific ion. Thus depending on design of the biosensor, the array may: (1) generally report a single product, indicating the presence or concentration of a single specific ion type: (2) generally report a single product, indicating the presence of numerous different specific ion types; or (3) specifically report different products, indicating the presence of numerous different specific ion types.

Methods of detecting fluorescent signals on a DNA chip are well known to those of skill in the art. In a preferred embodiment, the nucleic acid enzyme array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

A confocal microscope may be automated with a computer-controlled stage to automatically scan the entire high density array. Similarly, the microscope may be equipped with a phototransducer (e.g., a photomultiplier, a solid state array, a ced camera, etc.) attached to an automated data acquisition system to automatically record the fluorescence signal produced by each nucleic acid enzyme on the array. Such automated systems are described at length in U.S. Pat. No: 5,143,854 and PCT application 20 92/10092.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain like or similar results without departing from the spirit and scope of the invention.

Example 1

In Vitro Selection of a Ion-dependent Deoxyribozyme

This example demonstrates a method of creating nucleic acid enzymes that are dependent on the presence of an ion for activity. More specifically, use of a partially random DNA library to obtain deoxyribozymes that cleave RNA in the presence of $Zn^{2+}$ or $Co^{2+}$ is shown.

Materials and Methods Used in this Example
Oligonucleotides

DNA oligonucleotides were purchased from Integrated DNA Technologies Inc. Sequences of the random DNA template and the primers (P1, P2 and P3) used in PCR amplifications are listed below:

```
                                         (SEQ ID NO:3)
P1: 5'-GTGCCAAGCTTACCG-3'
                                         (SEQ ID NO:4)
P2: 5'-CTGCAGAATTCTAATACGACTCACTATAGGAAGAGATGGCGAC-
3'
                                         (SEQ ID NO:5)
P3: 5'-GGGACGAATTCTAATACGACTCACTATrA-3'
```

Template for Random DNA Pool:

```
                                         (SEQ ID NO:6)
5'-GTGCCAAGCTTACCGTCAC-N40-GAGATCTCGCCATCTCTTCCTA

TAGTGAGTCGTATTAG-3'
```

Primer P1b and P3b are the 5'-biotinylated version of primers P1 and P3. Primer P1a and P3a were prepared by 5'-labeling P1 and P3 with [□-$^{32}$P] ATP (Amersham) and T4 polynucleotide kinase (Gibco). The DNA/RNA chimeric substrate (17DS) for trans-cleavage assays has the sequence 5'-ACTCACTATrAGGAAGAGATG-3' (SEQ ID NO: 2), where rA denotes a single ribonucleotide. The all-RNA substrate (17RS) with the same sequence was purchased from Dharmacon Research Inc. The trans-cleaving deoxyribozyme 17E has the sequence 5'-CATCTCTTCTCCGAGCCGGTCGAAATAGTGAGT-3' (SEQ ID NO: 1). The deoxyribozyme named 17E1 is a variant of 17E with the sequence 5'-CATCTCTTTTGTCAGCGACTCGAAATAGTGA GT-3' (SEQ ID NO: 7). All oligonucleotides were purified using denaturing polyacrylamide get electrophoresis and desalted with the SepPak nucleic acid purification cartridges (Waters) before use.

Preparation of Random DNA Pool

The initial pool for DNA selection was prepared by template-directed extension followed by PCR amplification. The extension was carried out with 200 pmol of DNA template containing a 40-nucleotide random sequence region, and 400 pmol of primer P3b in 20×100 µl reaction mixtures for four thermal-cycles (1 min at 92° C., 1 min at 52° C., and 1 min at 72° C.). Reaction buffer also included 0.05 U/µl Taq polymerase (Gibco), 1.5 mM $MgCl_2$, 50 mM KCl, 10 mM Tris-HCl (pH 8.3 at 25° C.), 0.01% gelatin and 0.2 mM of each dNTP. Subsequently, 1 nmol each of P1 and P3b were added to the extension product to allow four more cycles of PCR amplification. The products were precipitated with ethanol and dissolved in 0.5 ml of buffer A, which contains 50 mM HEPES (pH 7.0), 500 mM (for Zn-DNA selection) or 1 M (for Co-DNA selection) NaCl. About 20 µM EDTA was also added to the buffer to chelate trace amount of divalent metal ion contaminants.

In Vitro Selection

The random DNA pool was immobilized on a NeutrAvidin column (Pierce) by incubating with the column materials for 30 minutes. The mixture was gently vortex-mixed a few times during the incubation. The unbound DNA strands were eluted with at least 5×100 µl of buffer A. The non-biotinylated strands of immobilized DNA were washed off the column with 5×100 µl of freshly prepared 0.2 M NaOH and 20 µM EDTA. The column was then neutralized with 5×100 µl of buffer A. The cleavage reaction was carried out by incubating the immobilized single-stranded DNA containing the single ribonucleotide (rA) with 3×20 µl of reaction buffer (buffer A plus 1 mM $ZnCl_2$ or $CoCl_2$) over 1 h. The eluted DNA molecules were pooled and precipitated with ethanol. A fraction of the selected DNA was amplified in 100 µl PCR reaction with 40 pmol each of primers P1 and P2 over 10–20 thermal cycles. One tenth of the PCR product was further amplified for six cycles with 50 pmol of primers P1 and P3b. The final PCR product was ethanol precipitated and used to initiate the next round of selection. During the selection of Zn(II)-dependent deoxyribozymes (called Zn-DNA hereafter), the concentration of $ZnCl_2$ was kept constant at 100 µM in the reaction buffer for the following rounds of selection. Reaction time was gradually decreased from 1 h to 30 s within 12 rounds of selection. For the selection of Co(II)-dependent deoxyribozymes (called Co-DNA hereafter), the concentration of $CoCl_2$ was gradually decreased from 1 mM to 100 µM and the reaction time from 1 h to 1 min within 10 rounds of selection. The twelfth generation of selectively amplified Zn-DNA and the tenth generation of Co-DNA were cloned using TA-TOPO Cloning Kit (Invitrogen) and sequenced with T7 Sequenase 2.0 Quick-denatured Plasmid Sequencing Kit (Amersham).

Reselection

Based on the sequence of class I Zn-DNA or Co-DNA, partially degenerate DNA template libraries for reselection were synthesized (Integrated DNA Technology Inc.) with 20% degeneracy at the N40 region. In other words, during the oligonucleotide synthesis of the N40 region, the wild type sequence was introduced at a probability of 80% at each position, while the other three nucleotides each occurred at a probability of 6.67%. The reselection pool was prepared with 10 pmol of template and 100 pmol of primers P1 and P3b using the same protocol previously described. With 10 pmol (number of molecules S=6×10$^{12}$) of partially randomized template, the statistic parameters of the DNA library used for reselection were calculated based on the following equations.

$$P(k,n,d)=[n!/(n-k)!k!]d^k(1-d)^{n-k} \quad (1)$$

$$N(k)=[n!/(n-k)!k!]3^k \quad (2)$$

$$C(n,k)=SP(k,n,d)/N(k) \quad (3)$$

P(k,n,d) is the probability of having k mutations within n (number of randomized positions, n=40) nucleotide positions that have been randomized at a degeneracy of d. N(k) is the number of distinct sequences that have k mutations with respect to the prototype sequence. C(n,k) is the number of copies for each sequence that has k mutations. The reselection pool was expected to contain the wild type sequence, all possible sequences with 1–8 point mutations, and a sampling of the sequences with >8 point mutations. More than half of the population contains ≧8 point-mutations. The protocol for reselection was the same as the primary selection, except that the reaction time was decreased from 20 min to 1 min and the concentration of ZnCl$_2$ or CoCl$_2$ was decreased from 20 μM to 5 μM over six generations. The sixth generation of reselected Zn- or Co-DNA were cloned and sequenced as previously described.

Kinetic Assays of the Reselected Cis-cleaving DNA

The 5'$^{32}$P-labeled precursor DNA for cis-cleavage assay was prepared by PCR-amplification of the selected DNA population or the cloned DNA plasmid with primer 1b and 3a. The double-stranded product was immobilized on a NeutrAvidin column through the biotin moiety on primer P1b. The catalytic strand of DNA was eluted off the column with 3×20 μl freshly prepared 0.2 N NaOH and neutralized with 8 μl of 3 M sodium acetate (pH 5.3) in the presence of 50 μg/ml bovine serum albumin (Sigma). Following ethanol precipitation, the single-stranded DNA was purified on an 8% denaturing polyacrylamide gel and desalted with SepPak nucleic acid purification cartridge. Bovine serum albumin (50 μg/ml) was added to the gel-soaking buffer (0.2 M NaCl, 20 μM EDTA, 10 mM Tris-HCl, pH 7.5) to prevent the DNA from adhering to the tube. The concentration of the DNA was determined by scintillation counting the radioactivity.

The precursor DNA was dissolved in buffer A and incubated at room temperature for 10 min before CoCl$_2$ or ZnCl$_2$ was added. The reaction was stopped with 50 mM EDTA, 90% formamide and 0.02% bromophenol blue. Reaction products were separated on an 8% denaturing polyacrylamide gel and quantified with a Molecular Dynamic phosphorimager.

In Vitro Selection of Zn(II)- or Co(II)-dependent Deoxyribozymes

The DNA molecules capable of cleaving an RNA bond in the presence of Co$^{2+}$ or Zn$^{2+}$ were obtained through in vitro selection. The initial DNA library for selection contains ~10$^{14}$ out of the possible 10$^{24}$(=4$^{40}$) DNA sequences. These molecules consist of a random sequence domain of 40 nucleotides flanked by two conserved primer-binding regions. The sequence of the conserved region was designed in such a way that they could form two potential substrate-binding regions (FIG. 1A). A ribonucleic adenosine was embedded in the 5'-conserved sequence region and was intended to be the cleavage site, since an RNA bond is more susceptible than a DNA bond toward hydrolytic cleavage. The intrinsic half-life of the phosphodiester linkage in RNA at pH 7 and 25° C. is estimated to be 1,000 years. The corresponding value for DNA is 200 million years.

The DNA pool was immobilized on a NeutrAvidin column through the biotin moiety on the 5' terminus of the DNA. Biotin and Avidin bind strongly with an association constant of K$_a$=10$^{15}$ M$^{-1}$. The sequences that underwent self-cleavage in the presence of Co$^{2+}$ or Zn$^{2+}$ were eluted off the column, amplified and used to seed the next round of selection (FIG. 1B). The selection stringency was increased during the selection process with shorter reaction time and less available divalent metal ions. The activity of the selected Zn-DNA gradually increased until the twelfth generation and declined thereafter, while the highest activity was achieved with the tenth generation of Co-DNA. Therefore the twelfth generation of Zn-DNA and the tenth generation of Co-DNA were cloned and sequenced. The cloned sequences can be divided into different classes based on sequence similarity (FIG. 2 and FIG. 3).

Individual sequences of the cloned Zn-DNA and Co-DNA were randomly chosen and sampled for activity. Under the selection conditions (100 μM Zn$^{2+}$, 500 mM NaCl, 50 mM HEPES, pH 7.0, 25° C.), the observed rate constants of Zn-DNAs from sequence-classes I and II were 0.1–0.2 min$^{-1}$, while class III sequences were less active, with k$_{obs}$ around 0.02 min$^{-1}$. The cleavage rate of the initial pool was 2×10$^{-7}$ min$^{-1}$. Therefore, a 10$^5$–10$^6$ fold increase in cleavage rate has been achieve for Zn-DNA selection. The cleavage rates of all the randomly picked Co-DNA sequences were <0.02 min$^{-1}$ under the conditions for Co-DNA selections (100 μM Co$^{2+}$, 1 M NaCl, 50 mM HEPES, pH 7.0, 25° C.). Interestingly, even in the buffer (1 M NaCl, 50 mM HEPES, pH 7.0) alone, the class II Co-DNA exhibited similar activity as in the presence of 100 μM Co$^{2+}$ or Zn$^{2+}$.

Clone #5 of Zn-DNA (Zn-5) and clone #18 of Co-DNA (Co-18) showed relatively high activity, as well as high frequency of occurrence, within their lineages. The k$_{obs}$ were 0.17 min$^{-1}$ for Zn-5 (in 100 μM Zn$^{2+}$) and 0.02 min$^{-1}$ for Co-18 (in 100 μM Co$^{2+}$). The sequences of Zn-5 and Co-18 were partially randomized (see Material and Methods for details) and subjected to reselection in order to further improve the reactivity and metal-binding affinity, and to explore the sequence requirement of the conserved catalytic motif. Based on equations (1)–(3), the reselection pool was expected to contain the wild type sequence, all possible sequences with 1–8 point mutations, and a sampling of the sequences with >8 point mutations. More than half of the population should contain ≧8 point mutations. Six rounds of reselection were carried out with 5–20 μM Zn$^{2+}$ or Co$^{2+}$, however the activity of the reselected DNA was similar to the activity of the wild type sequences. Sequencing of the Zn-DNA from both the initial selection and reselection revealed a highly conserved sequence region. Therefore the lack of activity improvement after reselection likely reflects a sequence pool dominated by a few highly reactive sequences.

Sequence Alignment and Structure Analysis of Zn-DNA

The sequences of thirty individual clones of initially selected Zn-DNA can be divided into three major classes based on sequence similarity. Differences among members of each class were limited to a few point mutations (FIG. 2). A highly conserved sequence region of 20 nt, 5'-TX$_1$X$_2$X$_3$AGCY$_1$Y$_2$Y$_3$TCGAAATAGT-3' (SEQ ID NO:8) (Region-20 nt), was observed in all but one sequence albeit at different locations. The sequences of 5'-$X_1X_2X_3$-3' and 3'-$Y_3Y_2Y_1$-5' are complimentary and covariant, indicating that they form base pair with each other:

5'-$X_1X_2X_3$-3'

3'-$Y_3Y_2Y_1$-5'

The secondary structures of the sequenced Zn-DNA were predicted using Zuker's DNA mfold program (see http://mfold.wustl.edu/~folder/dna/form1.cgi) through minimization of folding energy. The most stable structures predicted for those containing Region-20 nt all contained a similar structure motif. This common motif consists of a pistol-shaped three-way helical junction formed by a 3 bp hairpin, an 8 bp hairpin and a double helix linking to the rest of the molecule. The 3 bp hairpin and its adjacent single-stranded regions are part of the Region-20 nt. The ribonucleic adenosine is unpaired and positioned opposite of the 3 bp hairpin.

After reselection, twenty-eight Zn-DNA clones were sequenced (FIG. 4). When compared with the parental wild type sequence (class I Zn-DNA), the reselected Zn-DNA contained point mutations mostly outside of Region-20 nt. About one third of these sequences have a T→A mutation at position 73, converting the T-T mismatch in the wild type sequence to a Watson-Crick base pair. In one fourth of the reselected DNAs, the 5 nucleotide single-stranded bulge of the three-way junction has the sequence 5'-ACGAA-3', corresponding to 5'-TCGAA-3' in the wild type. Clone #17 (named ZnR17) of the reselected Zn-DNA is most active under selection conditions (FIG. 4). Structural analysis of ZnR17 revealed two completed base-paired helices in the three-way junction. Therefore, it was engineered into a trans-cleaving deoxyribozyme by deleting the sequences outside of the three-way junction and the loop of the 8 bp hairpin. Such truncation resulted in two individual stands, which hybridize with each other through two 9–10 bp helices. The strand containing the single ribonucleotide residue (rA) is considered as the substrate (named 17DS), while the other strand as the enzyme (named 17E). The catalytic core, which was highly conserved during selection, consists of a 3 bp hairpin and a 5 nt single-stranded bulge (FIG. 5).

Although ZnR17 was selected in $Zn^{2+}$, it does not contain structure motifs that were discovered in several Zn(II)-binding RNA molecules (Ciesiolka et al., 1995; Ciesiolka & Yarus, 1996). However, the conserved region of ZnR17 is very similar to that of the 8–17 deoxyribozymes selected by Santoro and Joyce using $Mg^{2+}$ as cofactor (Santoro & Joyce, 1997). The unpaired bulge region in the 8–17 DNA enzyme has the sequence 5'-WCGR-3' or 5'-WCGAA-3' (W=A or T; R=A or G). The highest activity was observed with the sequence containing 5'-TCGAA-3'. Among the Zn(II)-dependent deoxyribozymes obtained after reselection, 85% of them fell within the 5'-WCGAA-3' regime (W=A or T). However, the sequence of the two double helices flanking the catalytic core is different between the 8–17 (FIG. 6D) and the 17E deoxyribozymes (FIG. 6F), reflecting their different designs of the selection pool. Similar sequence motif was also observed in an RNA-cleaving deoxyribozyme (named Mg5) selected by Faulhammer and Famulok using 50 mM histidine and 0.5 mM $Mg^{2+}$ as cofactors (Faulhammer & Famulok, 1997). The homologous region in 31 out of the 44 sequenced clones had the sequence 5'-T$X_1X_2X_3$AGC$Y_1Y_2Y_3$ACGAA-3' (SEQ ID NO:9), falling within the WCGAA-3' regime. The authors predicted a secondary structure different from the 8–17 or 17E motif based on chemical modification analysis. However, a structure containing a three-way junction similar to that of the 17E and 8–17 deoxyribozymes is consistent with the chemical mapping results.

Sequence Alignment and Structure Analysis of Co-DNA

The sequences of the cis-cleaving deoxyribozyme selected in the presence of $Co^{2+}$ are more diverse than the Zn-DNA. They can be divided into three major classes based on sequence similarity (FIG. 3). There is no consensus sequence region among different classes. The secondary structure of each sequence class of Co-DNA was predicted with DNA mfold program. The minimal conserved sequence motif of class I Co-DNA includes a bulged duplex. The cleavage site is within the 13 nt single-stranded bulge. A 4 bp hairpin is also highly conserved and linked to the bulged duplex through 3 unpaired nucleotides. The folding of the sequences outside of this minimal motif was highly variable and resulted in structures with a wide range of stabilization energy.

The class II Co-DNA contains a sequence region (5'-ACCCAAGAAGGGGTG-3' (SEQ ID NO:10)) that was also found in an RNA-cleaving deoxyribozyme (termed G3) selected by Geyer and Sen (1997) (FIGS. 7A and 7B). The minimal motif predicted for class II Co-DNA shows similarity to that proposed for the G3 deoxyribozyme as well. The G3 deoxyribozyme was believed to be fully active in the absence of any divalent metal ions. Copious use of divalent metal chelating agents, such as EDTA, and accurate trace-metal analysis of the reaction solutions were used to rule out the need of the G3 deoxyribozyme for contaminating levels of divalent metals. As mentioned earlier, the activity of class II Co-DNA was the same in buffer alone or with added $Co^{2+}$ or $Zn^{2+}$, suggesting that this class of Co-DNA most likely contain the divalent metal-independent structure motif.

Effect of Metal Ions on the Activity of the Cis-Cleaving Deoxyribozymes

ZnR17 and Co-18 were examined for their activity dependence on monovalent ions and divalent metal ions other than $Zn^{2+}$ and $Co^{2+}$. In the presence of 1 mM EDTA and without added $Zn^{2+}$ ions, no cleavage was observed with ZnR17 even after two days, strongly suggesting that divalent metal ions are required for the activity of ZnR17. Although the cis-cleaving Zn-DNA was selected in the presence of 500 mM NaCl, NaCl was actually inhibitory to enzymatic activity. With 0–2 M NaCl added to the reaction buffer (100 $\mu$M $Zn^{2+}$, 50 mM HEPES, pH 7.0), $k_{obs}$ decreased with increasing NaCl concentration. The deleterious effect of NaCl was also manifested by lowered final percentage of cleavage products. For instance, only 50% of ZnR17 could be cleaved in the presence of 2 M NaCl even after long incubation times, while >95% of the DNA was cleavable in the absence of extra NaCl. Contrary to the Zn-DNA, the activity of Co-18 relies on NaCl and no cleavage was observed in the absence of NaCl. With 1 M NaCl, 8% of Co-18 molecules were cleaved within 5 min, while <0.2% were cleaved in the absence of extra NaCl.

Although the deoxyribozymes were selected using either zinc or cobalt as cofactor, they are also active in other transition metal ions and in $Pb^{2+}$. The cleavage efficiency of ZnR17 followed the trend of $Pb^{2+}$>$Zn^{2+}$>$Mn^{2+}$~$Co^{2+}$~$Ca^{2+}$>$Cd^{2+}$>>$Ni^{2+}$>$Mg^{2+}$. It is noteworthy that the cleavage rate in $Ca^{2+}$ was much higher than in $Mg^{2+}$, a similar trend was observed with the Mg5 deoxyribozyme. The order of Co-18 activity is as follow: $Zn^{2+}$>$Pb^{2+}$~$Co^{2+}$>$Ni^{2+}$>$Cd^{2+}$~$Mn^{2+}$>$Mg^{2+}$~$Ca^{2+}$. In general, both ZnR17 and Co-18 are more active in transition metal ions than in alkaline-earth metals, and higher activities were achieved with $Pb^{2+}$, $Co^{2+}$ and $Zn^{2+}$. The preference of the selected deoxyribozymes for $Co^{2+}$ and $Zn^{2+}$ reflected their selection criteria. A similar trend ($Pb^{2+}>Zn^{2+}>Mn^{2+}>Mg^{2+}$) was also observed with all four RNA-cleaving deoxyribozymes selected in parallel by Breaker and Joyce using one of the four metal ions ($Pb^{2+}$, $Zn^{2+}$, $Mn^{2+}$, $Mg^{2+}$) as cofactor (1995). The proposed secondary structures of the deoxyribozymes selected in $Pb^{2+}$ and $Mg^{2+}$ have been reported (Breaker & Joyce, 1994, 1995). No structure similarity was observed between ZnR17 and those RNA-cleaving deoxyribozymes.

Summary

Using in vitro selection technique, several groups of RNA-cleaving deoxyribozymes were isolated using $Zn^{2+}$ or $Co^{2+}$ as cofactor. No common sequence or structural features were observed between the Co(II)-dependent and the Zn(II)-dependent deoxyribozymes, in spite of the chemical similarities between these two transition metal ions. The deoxyribozymes selected in $Zn^{2+}$ share a common motif with the 8–17 and the Mg5 deoxyribozymes isolated under different conditions, including the use of different cofactors. Both the Co-DNA and the Zn-DNA exhibited higher activity in the presence of transition metal ions than in alkaline earth metal ions, which are the most commonly adopted metal cofactors by naturally occurring ribozymes.

Example 2

Deoxyribozyme as a Biosensor for $Pb^{2+}$ Detection

This Example describes a fluorescence-based biosensor for the detection of $Pb^{2+}$. The biosensor utilizes a deoxyribozyme developed in Example 1 (termed 17E) combined with fluorescence technology. Because catalytic activity, and therefore fluorescence, is dependent on $Pb^{2+}$, the biosensor provides real-time, quantitative, and sensitive measurements of $Pb^{2+}$ concentrations.

Materials and Methods used in this Example

Oligonucleotides

The oligonucleotides were purchased from Integrated DNA Technology Inc. The cleavable substrate (Rh-17DS-FD) is a DNA/RNA chimera with the sequence 5'-ACTCACTATrAGGAAGAGATG-3' (SEQ ID NO:2), in which rA represents a ribonucleotide adenosine. This RNA base is replaced with a DNA base for the non-cleavable substrate (Rh-17DDS-FD) (SEQ ID NO:11) used in the control experiment. Both substrates are covalently linked at the 5' end with 6-carboxyfluorescein (FAM) through NHS-ester conjugation and at the 3' end with DABCYL via CPG phosphoramidite. The deoxyribozyme (17E-Dy) is labeled at the 3'-end with DABCYL via CPG phosphoramidite and has the sequence 5'-CATCTCTTCTCCGAGCCGGTCGAAATAGTGAGT-3' (SEQ ID NO:1). All the oligonucleotides were purified by denaturing 20% polyacrylamide gel electrophoresis to ensure 100% labeling with the fluorescent dyes.

Fluorescence Spectroscopy

The enzyme-substrate complex was prepared with 50 nM each of 17E-Dy and Rh-17DS-FD in 50 mM NaCl and 50 mM Tris acetate (TA) buffer (pH 7.2) with a volume of 600 µl. The sample was heated at 80° C. for 5 min and cooled to 4° C. slowly to anneal the enzyme and substrate strands together. Fluorescence signal was collected by a FLA-3000G Multi-purpose 3-laser scanner for Fluorescence, Radioactivity and Macro Arrays (Fuji). The excitation laser wavelength was set at 473 nm and the filter was set at 520 nm to monitor the fluorescence of fluorescein. Steady state and slow-kinetic fluorescence were collected using a SLM 8000S photon counting fluorometer at ambient temperature. Excitation wavelength was fixed at 473 nm and emission was scanned from 500 to 650 nm. Polarization artifacts were avoided by using "magic angle" conditions. The steady-state emission spectra were collected from 460 to 500 nm ($\lambda_{ex}$= 473 nm). The time-dependent DNA enzyme catalyzed substrate cleavage was monitored at 473 nm at 2 s intervals. To initiate the reaction, 1–2 µl of concentrated divalent metal ion solution was injected into the cuvette using a 10 µl syringe while the DNA sample in the cuvette was constantly stirred.

DNA-based Sensor of Metal Ions

An in vitro selected DNA enzyme from Example 1 (termed 17E) that is capable of cleaving a lone RNA linkage within a DNA substrate (termed 17DS-FD) (FIG. 13A) was chosen for use as a DNA-based, fluorescent biosensor of metal ions. Assays of this enzyme indicate a highly $Pb^{2+}$ dependent activity with $k_{obs}$=6.5 $min^{-1}$ at pH 6.0 and $K_{apparent}$=13.5 µM. The biosensor was constructed by dual labeling the 5'-end of the substrate with the fluorophore 6-carboxyfluorescein (FAM) and, the 3'-end of the enzyme strand with DABCYL. This dual labeled substrate is named 17DS-FD. The 3'-end of the enzyme (17E) is also labeled with DABCYL. DABCYL serves as a universal fluorescence quencher. Steady-state fluorescence spectra were obtained by exciting the sample at 473 nm and scanning its emission from 500 to 650 nm.

When the substrate (17DS-FD) was hybridized to the enzyme strand (17E-Dy), the fluorescence of FAM was further quenched by the nearby additional DABCYL (FIG. 13B). Upon addition of $Pb^{2+}$, this quenching was eliminated and the fluorescence of FAM increased by ~660% over background fluorescence signals. Little change in the fluorescence signal occurred with addition of $Pb^{2+}$ to the substrate alone or to the complex of the enzyme and a non-cleavable DNA substrate with identical sequence. These findings show that the change in fluorescent signal with 17DS-FD/17E-Dy results from a DNA enzyme-atalyzed substrate cleavage, followed by product release.

The substrate cleavage reaction was monitored in real time with fluorescence spectroscopy. Like the ratiometric, anisotropy, or lifetime-based method, kinetic fluorescence measurement is independent of sampling conditions such as illumination intensity and sample thickness (Oehme & Wolfbeis, 1997). In order to determine the selectivity of the catalytic DNA sensor, a fluorescence image reader (Fuji) was used for real time monitoring of the cleavage reaction and product release using 7 different divalent metal ions. The activity of $Co^{2+}$, $Mg^{2+}$, $Zn^{2+}$, $Mn^{2+}$, $Cd^{2+}$ and $Ni^{2+}$ in cleaving the substrate strand was compared with $Pb^{2+}$ cleavage activity. These metal ions were chosen for comparison because in previous assays they demonstrated relatively high cleavage rates of 17E, while other metal ions were almost unreactive. The excitation laser wavelength of the fluorescence image reader was set to 473 nm and an emission filter was used to cut the wavelength to shorter than 520 nm. A 96-well plate was used as a reaction container. The first well of each row was set as an internal standard to quantify intensity and compare different scans. Therefore 5 µL of water were pipetted into the first well and 5 µL of the appropriate divalent metal ion were pipetted into the remaining wells.

Many different methods, such as comparing the cleavage rate constant or comparing initial reaction rate, may be used to assay the cleavage activity of the metal ions. One easy, practical way to monitor the reaction is by looking at the fluorescence intensity at a specific time interval, which conveniently eliminates the need for complicated data processing. Using this method, it was found that the fluorescence intensity after a 2 minute interval, showed high selectivity of the biosensor for $Pb^{2+}$. This selectivity is shown in FIG. 9A. Four different concentrations of metal ions were monitored using this method and in each case, $Pb^{2+}$ gave the highest fluorescence increase, indicating the fastest cleavage. To present data in a quantitative way, the darkness of each well was quantified and plotted in FIG. 9B. Besides $Pb^{2+}$, only $Zn^{2+}$ and $Co^{2+}$ showed any fluorescence increase at the 5 µM level.

Cleavage kinetics may be fitted into an exponential increase to a maximum wherein the initial stage of cleavage is considered linear. When comparing the relative fluorescence increases, the time interval does not have to be 2 minutes; any quantity of time in the linear range is suitable, and so long as it is kept the same for all the metal ions, the results should be consistent. Using this method, the present biosensor shows very high selectivity. For example, at low metal ion concentrations (500 nM), $Pb^{2+}$ is the only metal ion which causes the biosensor to produce a fluorescent signal. FIG. 9C shows the cleavage kinetics for all seven metal ions in a time course of 90 minutes. $Pb^{2+}$ was the only ion to produce a fluorescence signal; all other metal ions produced signals similar to the background, demonstrating that the signal response to $Pb^{2+}$ was not affected by the presence of equal amounts of other ions, indicating that this biosensor is well suited for selective monitoring of $Pb^{2+}$ in the presence of other metal ions.

The $Pb^{2+}$ detection range is from 100 nM to 5 µM, if the fluorescence increase after 2 minutes of reaction is counted. However, when lead concentration is higher than 5 µM, the signal is saturated. To avoid saturation of the signal, dilution must be done on more concentrated $Pb^{2+}$ samples before an accurate concentration can be derived. Respectively, $Zn^{2+}$ and $Co^{2+}$ showed the second and third highest signal response, and are considered interference ions. However, when the concentration is below 5 µM, the biosensor has almost no response to them.

Fluorescence of the New Biosensor Versus Fluorescence of the Biosensor Disclosed in U.S. application Ser. No. 09/605,558, now U.S. Pat. No. 6,706,474

When the temperature is increased from 4° C. to room temperature (23° C.), the biosensor of U.S. application Ser. No. 09/605,558. now U.S. Pat. No. 6,706,474 shows a significant decrease in fluorescence signal (from 400% signal to backgroun ratio to 60% signal to background ratio), due to the partial "melting" of the substrate-enzyme duplex. Therefore when utilizing these biosensors, it is important to know the melting profile of the enzyme-substrate duplex. Two methods may be used to determine the melting temperature of the duplex. One method is based on the hyperchromatic property of DNA. By monitoring the absorption at 260 nm with increases of temperature, the melting temperature can be obtained. Using this method, the melting temperature of 17DS-FD/17E-DY duplex was determined to be 35° C.

A second method for determining melting temperatures takes advantage of the fluorescent properties of the 17DS-FD/17E-DY duplex. The substrate strand used is non-cleavable FI-17DDS (17DDS with a FAM attached to the 5' end), and the enzyme strand is 17E-DY (17E with DABCYL attached to the 3' end). When the two strands are annealed, the fluorescence from FAM is quenched by DABCYL. The fluorescence is recovered when the duplex melts. By monitoring the FAM fluorescence at 520 nm, the melting curve of the DNA can be acquired. The melting temperature determined by this method is 34° C. The results from the two different methods are similar, indicating that the coupling of the fluorophore to the DNA does not change the stability of the duplex.

Example 3

DNA Chip Comprising an Array of Nucleic Acid Enzymes

This prophetic example describes the production of and use of a DNA chip for sensing ions, in particular heavy metal ions.

The first step towards the application of deoxyribozymes in heavy metal sensing is to obtain various deoxyribozymes with different metal specificity and affinity. In vitro selection will be carried out to isolate a variety of deoxyribozymes. A detailed description of the selection protocol can be found in Example 1. Each family of deoxyribozyme will be specific for different divalent metal ions (e.g. $Pb^{2+}$, $Hg^{2+}$, $Zn^{2+}$, $Co^{2+}$, $Cd^{2+}$, $Ni^{2+}$, $Mn^{2+}$, etc). Within each family, different sequences will have different affinities of the specified metal ion.

These deoxyribozymes and their substrates will then be arrayed onto a DNA chip with one dimension for metal ion specificity and the other for affinity of the corresponding metal (FIG. 11). The enzyme strands immobilized on the chip at 3'-ends can be synthesized on the chip using photolithographic methods (Fodor et al., 1991; Pease et al., 1994) or can be synthesized off-chip and then attached to the chip using various methods (Joos et al., 1997; O'Donnell-Maloney et al., 1997; Guschin et al., 1997). The 3'-ends of the enzyme and substrate strands will be labeled with a fluorescence quencher, which can be a fluorescent or non-fluorescent moiety. The 5' end of the substrate will be labeled with a fluorophore. Guanidine base may be used, for example, as an efficient quencher of fluorescein.

Hybridization of the enzyme and substrate will result in the quenching of the donor fluorescence. Upon exposure to the sample containing the active metal ion, the substrate will be cleaved and products will dissociate, resulting in strong fluorescence of the dye attached to the enzyme strand. The metal ion species can be qualitatively identified based on the metal specificity of different families of deoxyribozymes. A hypothetical sample result is shown in FIG. 11B. The pattern of fluorescence intensity shows that there are three kinds of metal (M1, M4, and M6) in the sample.

The concentration of the metal ion under inspection can be quantified with deoxyribozymes with different metal affinity. Given a certain concentration of the metal ion, different sequences within the same family will have different cleavage efficiencies due to their different thresholds in response to the metal concentration. The metal concentration applied may exceed the saturation concentration of those having higher affinity; therefore full cleavage will occur within a certain time and present strong fluorescence. On the other hand, the substrates of those with lower affinity will only be partly cleaved and emit weaker fluorescence. The sample hypothetical result shown in FIG. 11B shows high (c1), medium (c4), and low (c6) concentrations of M1, M4, and M6, respectively.

The fluorescence patterns with respect to different deoxyribozyme sequences will be compared with standard calibration maps. After de-convolution of the fluorescence pattern, direct information can be obtained about the identity and concentration of metal ions in the samples.

References

Bogden, J. D.; Louria, D. B. *Bull. Environ. Contam. Toxicol.* 1975, 14:289–94.

Breaker, R. R.; Joyce, G. F. *Chem. Biol.* 1995, 2, 655–660.

Breaker, R. R. & Joyce, G. F. A DNA enzyme that cleaves RNA. *Chem. Biol.* 1, 223–229 (1994).

Breaker, R. R. DNA enzymes. *Nat. Biotechnol.* 15, 427–431 (1997).

Cadwell, R. C.; Joyce, G. F. *PCR Methods Appl.* 1992, 2, 28–33.

Cadwell, R. C.; Joyce, G. F. *PCR Methods Appl.* 1994, 3, S136–S140.

Carmi, N., Shultz, L. A. & Breaker, R. R. In vitro selection of self-cleaving DNAs. *Chem. Biol.* 3, 1039–1046 (1996).

Chapman, K. B.; Szostak, J. W. *Curr. Opin. Struct. Biol.* 1994, 4, 618–622.

Ciesiolka, J.; Gorski, J.; Yarus, M. *RNA* 1995, 1, 538–550.

Ciesiolka, J.; Yarus, M. *RNA* 1996, 2, 785–793.

Conaty, J.; Hendry, P.; Lockett, T. *Nucleic Acids Res.* 1999, 27, 2400–2407.

Conn, M. M.; Prudent, J. R.; Schultz, P. G. *J. Am. Chem. Soc.* 1996, 118, 7012–7013.

Cuenoud, B. & Szostak, J. W. A DNA metalloenzyme with DNA ligase activity. *Nature* 375, 611–614 (1995).

Czarnik, A. W. Desperately seeking sensors. *Chem. Biol.* 2, 423–428 (1995).

Dai, X.; De Mesmaeker, A.; Joyce, G. F. *Science* 1995, 267, 237–240.

Deo, S. & Godwin, H. A. A Selective, Ratiometric Fluorescent Sensor for $Pb^{2+}$. 2000, *J. Am. Chem. Soc.* 122, 174–175.

Didenko, V. V. i BioTechniques 2001, 31:1106–21.

Earnshaw & Gait, "Modified Oligoribonucleotides as site-specific probes of RNA structure and function," *Biopolymers* (John Wiley & Sons, Inc.) 48:39–55, 1998.

Ekland, E. H.; Szostak, J. W.; Bartel, D. P. *Science* 1995, 269, 364–370.

Ekland, E. H.; Bartel, D. P. *Nature* 1996, 382, 373–376.

Famulok, M. *Curr. Opin. Struct. Biol.* 1999, 9, 324–329.

Faulhammer, D.; Famutok, M. *Angew. Chem., Int. Ed. Engl.* 1997, 35, 2837–2841.

Fodor, S. P. A., Read, J. L., Pirrung, M. C., Stryer, L., Lu, A. T. & Sotas, D. (1991). Light-directed, spatially addressable parallel chemical synthesis. *Science* 251: 767–773.

Frank, D. N.; Pace, N. R. *Proc. Natl. Acad. Sci. U.S.A.* 1997, 94, 14355–14360.

Geyer, C. R.; Sen, D. *Chem. Biol.* 1997, 4, 579–593.

Godwin, H. A. & Berg, J. M. A Fluorescent Zinc Probe Based on Metal-Induced Peptide Folding. *J. Am. Chem. Soc.* 118, 6514–6515 (1996).

Guschin, D., Yershov, G., Zaslavsky, A., Gemmell, A., Shick, V., Proudnikov, D., Arenkov, P. & Mirzabekov, A. (1997). Manual manufacturing of oligonucleotide, DNA, and protein microchips. *Anal. Biochem.* 250: 203–211.

Hennrich, G.; Sonnenschein, H.; Resch-Genger, U. *J. Am. Chem. Soc.* 1999, 121, 5073–5074.

Illangasekare, M.; Yarus, M. *J. Mol. Biol.* 1997, 268, 631–639.

Imperiali, B., Pearce, D. A., Sohna, J. -E., Walkup, G. & Torrado, A. Peptide platforms for metal ion sensing. *Proc. SPIE-Int. Soc. Opt. Eng.* 3858, 135–143 (1999).

Jhaveri, et al., Designed Signaling Aptamers that Transduce Molecular Recognition to Changes in Fluorescence Intensity, *Journal of the American Chemical Society;* 2000; 122(11); 2469–2473.

Joos, B., Kuster, H. & Cone, R. (1997). Covalent attachment of hybridizable oligonucleotides to glass supports. *Anal. Biochem.* 247: 96–101.

Joyce, G. F. *Curr. Opin. Struct. Biol.* 1994, 4, 331–336.

Koizumi, M.; Soukup, G. A.; Kerr, J. N. Q.; Breaker, R. R. *Nat. Struct. Biol.* 1999, 6, 1062–1071.

Lakowicz, J. R. In *Principles of Fluorescence Spectroscopy;* 2nd ed.; Kluwer Academic/Plenum: New York, 1999.

Lee, M., & Walt, D. R. A fiber-optic microarray biosensor using aptamers as receptors. *Anal Biochem* 282(1):142–146, 2000.

Lehman, N.; Joyce, G. F. *Nature* 1993, 361, 182–185.

Li, J., Zheng, W., Kwon, A. H. & Lu, Y. In vitro selection and characterization of a highly efficient Zn(II)-dependent RNA-cleaving deoxyribozyme. *Nucleic Acids Res.* 28, 481–488 (2000).

Li, Y.; Sen, D. *Nat. Struct. Biol.* 1996, 3, 743–747.

Li, Y.; Breaker, R. R. *Proc. Natl. Acad. Sci. U.S.A.* 1999, 96, 2746–2751.

Li, Y.; Liu, Y.; Breaker, R. R. *Biochemistry* 2000, 39, 3106–3114.

Lohse, P. A.; Szostak, J. W. *Nature* 1996, 381, 442–444.

Lorsch, J. R.; Szostak, J. W. *Nature* 1994, 371, 31–36.

Marcus, A. H.; Elias, R. W. *ASTM Spec. Tech. Publ.* 1995, STP 1226: 12–23.

Miyawaki, A., et al. Fluorescent indicators for $Ca^{2+}$ based on green fluorescent proteins and calmodulin. *Nature* 388, 882–887 (1997).

O'Donnell-Maloney, M. J., Tang, K., Koester, H., Smith, C. L. & Cantor, C. R. (1997). High-Density, Covalent Attachment of DNA to Silicon Wafers for Analysis by MALDI-TOF Mass Spectrometry. *Anal. Chem.* 69: 2438–2443.

Oehme, I. & Wolfbeis, O. S. Optical sensors for determination of heavy metal ions. *Mikrochim. Acta* 126, 177–192 (1997).

Pan, T. & Uhlenbeck, O. C. A small metalloribozyme with a two-step mechanism. *Nature* 358, 560–563 (1992).

Pan, T.; Dichtl, B.; Uhlenbeck, O. C. *Biochemistry* 1994, 33, 9561–9565.

Pearce, D. A.; Walkup, G. K.; Imperiali, B. *Bioorg. Med. Chem. Lett.* 1998, 8, 1963–1968.

Pease, A. C., Solas, D., Sullivan, E. J., Cronin, M. T., Holmes, C. P. & Fodor, S. P. A. (1994). Light-generated oligonucleotide arrays for rapid DNA sequence analysis. *Proc. Natl. Acad. Sci. U.S.A.* 91: 5022–5026.

Piccirilli, J. A.; McConnell, T. S.; Zaug, A. J.; Noller, H. F.; Cech, T. R. *Science* 1992, 256, 1420–1424.

Pley, H. W.; Flaherty, K. M.; McKay, D. B. *Nature* 1994, 372, 68–74.

Potyrailo, R. A.; Conrad, R. C.; Ellington, A. D.; Hieftje, G. M. *Anal. Chem.* 1998, 70, 3419–3425.

Potyrailo, R. A., Conrad, R. C., Ellington, A. D. & Hieftje, G. M. (1999). Adapting Selected Nucleic Acid Ligands (Aptamers) to Biosensors. *Anal. Chem.* 70: 3419–3425.

Prudent, J. R.; Uno, T.; Schultz, P. G. *Science* 1994, 264, 1924–1927.

Rabinowitz, M.; Leviton, A.; Bellinger, D. *Am. Jour. Public Health Field April* 1985, 75: 403–4.

Robertson, M. P.; Ellington, A. D. *Nat. Biotechnol.* 1999, 17, 62–66.

Robertson, M. P.; Ellington, A. D. *Nucleic Acids Res.* 2000, 28, 1751–1759.

Roth, A.; Breaker, R. R. *Proc. Natl. Acad. Sci. U.S.A.* 1998, 95, 6027–6031.

Rurack, K., Kollmannsberger, M., Resch-Genger, U. & Daub, J. A Selective and Sensitive Fluoroionophore for HgII, AgI, and CuII with Virtually Decoupled Fluorophore and Receptor Units. *J. Am. Chem. Soc.* 122, 968–969 (2000).

Santoro, S. W.; Joyce, G. F. *Proc. Natl. Acad. Sci. U.S.A.* 1997, 94, 4262–4266.

Santoro, S. W., Joyce, G. F., Sakthivel, K., Gramatikova, S. & Barbas, C. F., III RNA Cleavage by a DNA Enzyme with Extended Chemical Functionality. *J. Am. Chem. Soc.* 122, 2433–2439 (2000).

Schwartz, J.; Levin, R. *Env. Research Field.* 1991, February 54: 1–7.

Scott, W. G.; Finch, J. T.; Klug, A. *Cell* 1995, 81, 991–1002.

Tang and Breaker, *Proc. Natl. Acad. Sci. USA*, 97, 5784–5789 (2000).

Tarasow, T. M.; Tarasow, S. L.; Eaton, B. E. *Nature* 1997, 389, 54–57.

Thompson, R. B., Maliwal, B. P., Feliccia, V. L., Fierke, C. A. & McCall, K. Determination of Picomolar Concentrations of Metal Ions Using Fluorescence Anisotropy: Biosensing with a "Reagentless" Enzyme Transducer. *Anal. Chem.* 70, 4717–4723 (1998).

Tsang, J.; Joyce, G. F. *Methods Enzymol.* 1996, 267, 410–426.

Tsien, R. Y. Fluorescent and photochemical probes of dynamic biochemical signals inside living cells in *Fluorescenct Chemosensors for Ion and Molecule Recognization* (ed. Czarnik, A. W.) 130–46 (American Chemical Society, Washington, D.C., 1993).

Tuerk, C.; Gold, L. *Science* 1990, 249, 505–510.

Tyagi S.; Kramer, F. R. *Nat. Biotechnol.* 1996 14, 303.

Tyagi, S.; Bratu, D. P.; Kramer, F. R. *Nat. Biotechnol.* 1998, 16:49–58.

Tyagi, S.; Marras, S. A. E.; Kramer, F. R. *Nat. Biotechnol.* 2000, 18:1191–6.

Uphoff, K. W.; Bell, S. D.; Ellington, A. D. *Curr. Opin. Struct. Biol.* 1996, 6, 281–288.

Vaish, N. K.; Heaton, P. A.; Fedorova, O.; Eckstein, F. *Proc. Natl. Acad. Sci. U.S.A.* 1998, 95, 2158–2162.

Walkup, G. K. & Imperiali, B. Design and Evaluation of a Peptidyl Fluorescent Chemosensor for Divalent Zinc. *J. Am. Chem. Soc.* 118, 3053–3054 (1996).

Wecker, M.; Smith, D.; Gold, L. *RNA* 1996, 2, 982–994.

Wiegand, T. W.; Janssen, R. C.; Eaton, B. E. *Chem. Biol.* 1997, 4, 675–683.

Wilson, C.; Szostak, J. W. *Nature* 1995, 374, 777–782.

Winkler, J. D., Bowen, C. M. & Michelet, V. Photodynamic Fluorescent Metal Ion Sensors with Parts per Billion Sensitivity. *J. Am. Chem. Soc.* 120, 3237–3242 (1998).

Wittmann, C., Riedel, K. & Schmid, R. D. Microbial and Enzyme sensors for environmental monitoring. *Handb. Biosens. Electron. Noses,* 299–332 (1997).

Zhang, B.; Cech, T. R. *Nature* 1997, 390, 96–100.

Zillmann, M.; Limauro, S. E.; Goodchild, J. *RNA* 1997, 3, 734–747.

---

What is claimed is:

1. A method of determining the concentration of a metal ion in the presence of other ions, in a sample, comprising:
   detecting the metal ion in the sample by a method comprising
   forming a mixture comprising:
   (1) a nucleic acid enzyme,
   (2) the sample, and
   (3) a substrate,
   to produce a product from the mixture; and
   determining the presence of the product;
   wherein the enzyme comprises at least one quencher and is dependent on the metal ion as a cofactor to produce the product from the substrate,
   the substrate comprises a ribonucleotide, a deoxyribonucleotide, or both, and
   the substrate comprises at least one fluorophore and at least one quencher; and
   determining the concentration of the metal ion by measuring an amount of the product produced.

2. The method of claim 1, wherein the nucleic acid enzyme and the substrate comprise separate nucleic acid strands.

3. The method of claim 1, wherein a 5' end of the substrate comprises a first fluorophore and a 3' end of the substrate comprises a first quencher for the fluorophore and wherein a 3' end of the enzyme comprises a second quencher for the fluorophore.

4. The method of claim 3, wherein the fluorophore is 6-carboxyfluorescein (FAM) and wherein the first and second quenchers are 4-(4'-(dimethylaminophenylazo)benzoic acid) (DABCYL).

5. The method of claim 1, wherein the enzyme is linked to a support.

6. The method of claim 1, wherein the substrate comprises a nucleic acid of SEQ ID NO: 2.

7. The method of claim 1, wherein the enzyme comprises a nucleic acid of SEQ ID NO: 1.

8. The method of claim 1, wherein the ion is $Co^{2+}$.

9. The method of claim 1, wherein the ion comprises a member selected from the group consisting of Mg(II), Ca(II), Mn(II), Co(II), Ni(II), Zn(II) and Pb(II).

10. The method of claim 1, wherein the ion is selected from the group consisting of $Mg^{2+}$, $Ca^{2+}$, $Mn^{2+}$, $Co^{2+}$, $Ni^{2+}$, $Zn^{2+}$ and $Pb^{2+}$.

11. The method of claim 10, wherein the ion is $Pb^{2+}$.

12. The method of claim 1, wherein the metal ion is $Zn^{2+}$.

13. The method of claim 1, wherein the metal ion is $Ca^{2+}$.

14. The method of claim 1, wherein the sample suspected of containing the ion comprises a bodily fluid.

15. The method of claim 14, wherein the bodily fluid is blood.

16. The method of claim 1, wherein the nucleic acid enzyme is part of an array.

* * * * *